(12) United States Patent
Brockhaus et al.

(10) Patent No.: US 11,313,864 B2
(45) Date of Patent: Apr. 26, 2022

(54) METHOD FOR DETERMINING ANTI-DRUG ANTIBODIES IN A MINIPIG SAMPLE

(71) Applicant: Hoffmann-La Roche Inc., Little Falls, NJ (US)

(72) Inventors: Janis Brockhaus, Penzberg (DE); Astrid Reiser, Penzberg (DE); Mirko Ritter, Penzberg (DE); Kay-Gunnar Stubenrauch, Penzberg (DE); Rudolf Vogel, Penzberg (DE); Markus Zadak, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 262 days.

(21) Appl. No.: 16/783,623

(22) Filed: Feb. 6, 2020

(65) Prior Publication Data
US 2020/0309786 A1 Oct. 1, 2020

Related U.S. Application Data

(63) Continuation of application No. PCT/EP2018/071337, filed on Aug. 7, 2018.

(30) Foreign Application Priority Data

Aug. 8, 2017 (EP) .................................... 17185220

(51) Int. Cl.
| | |
|---|---|
| C07K 16/46 | (2006.01) |
| C07K 16/00 | (2006.01) |
| G01N 33/53 | (2006.01) |
| G01N 33/68 | (2006.01) |
| C07K 16/18 | (2006.01) |
| G01N 33/543 | (2006.01) |

(52) U.S. Cl.
CPC ......... *G01N 33/6854* (2013.01); *C07K 16/18* (2013.01); *G01N 33/543* (2013.01); *C07K 2317/20* (2013.01); *C07K 2317/33* (2013.01); *C07K 2317/565* (2013.01)

(58) Field of Classification Search
None
See application file for complete search history.

(56) References Cited

U.S. PATENT DOCUMENTS 9,933,433 B2 * 4/2018 Essig ..................... C07K 16/42

FOREIGN PATENT DOCUMENTS

| WO | 2008/031532 A1 | 3/2008 |
| WO | 2012/022682 A1 | 2/2012 |

OTHER PUBLICATIONS

Bruck et al. et al., "Purification of mouse monoclonal antibodies from ascitic fluid by DEAE Affi-Gel Blue chromatography" Methods Enzymol. 121:587-596 ( 1986).
Burdon and Knippenbert et al., "Preparation of enzyme-antibody or other enzyme-macromolecule conjugates" Elsevier, Amsterdam:221-278 ( 1990).
Campbell Laboratory Techniques in Biochemistry and Mol. Biol. Burdon et al., Amsterdam:Elsevier Science Publishers, vol. 13 ( 1985).
Chothia et al., "Canonical structures for the hypervariable regions of immunoglobulins" J Mol Biol 196(4):901-917 (Apr. 23, 1987).
Geng et al., "Validation of immunoassays used to assess immunogenicity to therapeutic monoclonal antibodies" J. Pharm. Biomed. Anal. 39:364-375 ( 2005).
Groner et al., "Therapeutic Antibodies" Current Molecular Medicine 4:539-547 ( 2004).
Gutierrez et al., "Quantifying by monoclonal antibodies of specific IgG, IgM and IgA in the serum of minipigs experimentally infected with Actinobacillus pleuropneumoniae" Research in Veterinary Science 53:254-256 ( 1992).
Harris et al., "Monoclonal antibodies as therapeutic agents for cancer" Lancet Oncol 5:292-302 ( 2004).
He et al., "Evaluation of the efficacy of a recombinant Entamoeba histolytica cysteine proteinase (EhCP112) antigen in minipig" Experimental Parasitology 131:258-260 ( 2012).
International Preliminary Report on Patentability (IPRP) for PCT/EP2018/071337 dated Feb. 11, 2020.
International Search Report for PCT/EP2018/071337 dated Sep. 20, 2018.
Kaliyaperumal et al., "Immunogenicity Assessment of Therapeutic Proteins and Peptides" Current Pharmaceutical Biotechnology 10:352-358 ( 2009).
Klein et al., "Progress in overcoming the chain association issue in bispecific heterodimeric IgG antibodies" mABs 4:653-663 ( 2012).
Lefranc et al., "IMGT, the international ImMunoGeneTics database" Nucleic Acids Research 27(1):209-2012 ( 1999).
Levene et al., "Therapeutic monoclonal antibodies in oncology" J R Soc Med 98:146-152 ( 2005).
MacCallum et al., "Antibody-antigen interactions: contact analysis and binding site topography" J Mol Biol 262(5):732-745 (Oct. 11, 1996).
Mire-Sluis et al., "Recommendations for the design and optimization of immunoassays used in the detection of host antibodies against biotechnology products" J Immunol Methods 289:1-16 ( 2004).
Pan et al., "Anti-idiotypic antibodies: biological function and structural studies" FASEB 9:43-49 ( 1995).
Pearson, W.R., "Effective Protein Sequence Comparison" Method Enzymol 266:227-258 (Jan. 1, 1996).

(Continued)

*Primary Examiner* — Maher M Haddad
(74) *Attorney, Agent, or Firm* — Jonathan P. Aumais

(57) ABSTRACT

The present invention relates to in vitro methods for determining the presence or absence of an anti-drug antibody (ADA) or drug/ADA immunecomplexes in a minipig sample. The invention further relates to antibodies specifically binding to minipig IgG that are applicable in the methods of the invention.

15 Claims, 7 Drawing Sheets

Specification includes a Sequence Listing.

(56) References Cited

OTHER PUBLICATIONS

Pearson, W.R., et al., "Comparison of DNA Sequences with Protein Sequences" Genomics 46:24-36 (Aug. 25, 1997).
Pearson, W.R., et al., "Improved tools for biological sequence comparison" PNAS 85:2444-2448 (Apr. 1, 1988).
Shankar et al., "Recommendations for the validation of immunoassays used for detection of host antibodies against biotechnology products" J Pharm Biomed Anal. 48:1267-1281 ( 2008).
Van Mierlo et al., "The Göttingen minipig® as an alternative non-rodent species for immunogenicity testing: A demonstrator study using the IL-1 receptor antagonist anakinra" Journal of Immunotoxicology 10(1):96-105 ( 2013).
Van Mierlo et al., "The minipig as an alternative non-rodent model for immunogenicity testing using the TNFα blockers adalimumab and infliximab" J Immunotoxicol 11(1):62-71 ( 2014).

* cited by examiner

METHOD FOR DETERMINING ANTI-DRUG ANTIBODIES IN A MINIPIG SAMPLE

CROSS REFERENCE TO RELATED APPLICATIONS

This application is a continuation of International Application No. PCT/EP2018/071337, filed Aug. 7, 2018, which claims priority to European Patent Application No. 17185220.5, filed Aug. 8, 2017, which are incorporated herein by reference in its entirety.

SEQUENCE LISTING

This application contains a Sequence Listing which has been submitted electronically in ASCII format and is hereby incorporated by reference in its entirety. Said ASCII copy, created on Jan. 22, 2020, is named P34342-US-Sequence-Listing.txt and is 11,952 bytes in size.

FIELD OF THE INVENTION

The present invention relates to an in vitro method for determining anti-drug antibodies in a minipig sample, and antibodies specifically binding to minipig IgG.

BACKGROUND OF THE INVENTION

The clinical development of novel therapeutic antibodies requires the evaluation of their potential immunogenicity by appropriate assays (Kaliyaperumal, A. and Jing, S., Curr. Pharm. Biotechnol. 10 (2009) 352-358). The anti-drug antibody (ADA) testing usually involves a two tier approach: (1) assays for ADA detection and (2) assays for ADA characterization. ADA detection assays include screening and specificity confirmation (confirmatory) assays. Microtiter plate-based enzyme-linked immunosorbent assays (ELISAs) are the most widely used format to screen for ADAs due to their high-throughput efficiency, simplicity and high sensitivity (Geng, D., et al., J. Pharm. Biomed. Anal. 39 (2005) 364-375). ADA ELISAs are most often designed in a bridge format which provides high selectivity, detection of all isotypes and pan-species ADA detection capability (Mire-Sluis, A. R., et al., J. Immunol. Methods 289 (2004) 1-16). An ADA ELISA for detecting ADAs in samples derived from monkey species is disclosed in WO 2008031532 A1.

SUMMARY OF THE INVENTION

The present invention relates to an in vitro method for determining the presence or absence of an anti-drug antibody (ADA) in a minipig sample, the method comprising:
  contacting the sample with an excess amount of a drug to which the ADA binds to form drug/ADA complexes,
  contacting the drug/ADA complexes with an antibody specifically binding minipig IgG, wherein the antibody specifically binding to minipig IgG does not specifically bind to human IgG,
  determining the binding of the antibody specifically binding to minipig IgG to the drug/ADA complexes to determine whether ADA is present in the sample.

In another aspect the invention relates to an in vitro method for determining the presence or absence of immune complexes comprising a drug and an antibody specifically binding to the drug (drug/ADA complexes) in a minipig sample, the method comprising:

a) contacting the minipig sample with an immobilized antibody that specifically binds to the drug to immobilize the drug/ADA complexes present in the minipig sample,
b) contacting the drug/ADA complexes with an antibody specifically binding minipig IgG, wherein the antibody specifically binding to minipig IgG does not specifically bind to human IgG, and
c) determining the binding of the antibody specifically binding to minipig IgG to the drug/ADA complexes to determine whether ADA is present in the sample.

In one embodiment of the invention the antibody specifically binding to minipig IgG does not specifically bind to human IgG. In one embodiment of the invention the antibody specifically binding to minipig IgG does not specifically bind to mouse IgG.

In one embodiment of the invention the antibody specifically binding to minipig IgG specifically binds to the Fc domain of minipig IgG. In one embodiment the antibody specifically binding to the Fc domain of minipig IgG comprises a CDR1 of the heavy chain of SEQ ID NO: 3, a CDR2 of the heavy chain of SEQ ID NO: 4, and a CDR3 of the heavy chain of SEQ ID NO: 5, a CDR1 of the light chain of SEQ ID NO: 6, a CDR2 of the light chain of SEQ ID NO: 7, and a CDR3 of the light chain of SEQ ID NO: 8 (corresponding to the six CDRs of the antibody "2.8.14" as disclosed herein).

In one embodiment of the invention the antibody specifically binding to minipig IgG specifically binds to the Fab domain of minipig IgG. In one embodiment the antibody specifically binding to the Fab domain of minipig IgG comprises a CDR1 of the heavy chain of SEQ ID NO: 11, a CDR2 of the heavy chain of SEQ ID NO: 12, and a CDR3 of the heavy chain of SEQ ID NO: 13, a CDR1 of the light chain of SEQ ID NO: 14, a CDR2 of the light chain of SEQ ID NO: 15, and a CDR3 of the light chain of SEQ ID NO: 16 (corresponding to the six CDRs of the antibody "1.2.6" as disclosed herein). In one embodiment the antibody specifically binding to the Fab domain of minipig IgG comprises a CDR1 of the heavy chain of SEQ ID NO: 19, a CDR2 of the heavy chain of SEQ ID NO: 20, and a CDR3 of the heavy chain of SEQ ID NO: 21, a CDR1 of the light chain of SEQ ID NO: 22, a CDR2 of the light chain of SEQ ID NO: 23, and a CDR3 of the light chain of SEQ ID NO: 24 (corresponding to the six CDRs of the antibody "2.3.8" as disclosed herein). In one embodiment the antibody specifically binding to the Fab domain of minipig IgG comprises a CDR1 of the heavy chain of SEQ ID NO: 27, a CDR2 of the heavy chain of SEQ ID NO: 28, and a CDR3 of the heavy chain of SEQ ID NO: 29, a CDR1 of the light chain of SEQ ID NO: 30, a CDR2 of the light chain of SEQ ID NO: 31, and a CDR3 of the light chain of SEQ ID NO: 32 (corresponding to the six CDRs of the antibody "2.11.16" as disclosed herein).

In one embodiment of the invention the drug is a drug antibody (DA).

In one embodiment of the invention the method is a sandwich assay, wherein in step a) the drug/ADA complexes are contacted with an antibody specifically binding to human IgG, wherein the antibody specifically binding to human IgG is immobilized on a support, thereby immobilizing the drug/ADA complexes on the support, and wherein the immobilized drug/ADA complexes are subsequently contacted with the antibody specifically binding to minipig IgG according to step b).

Another aspect of the invention is an antibody specifically binding to minipig IgG, comprising a CDR1 of the heavy chain of SEQ ID NO: 3, a CDR2 of the heavy chain of SEQ ID NO: 4, and a CDR3 of the heavy chain of SEQ ID NO: 5, a CDR1 of the light chain of SEQ ID NO: 6, a CDR2 of the light chain of SEQ ID NO: 7, and a CDR3 of the light chain of SEQ ID NO: 8 (corresponding to the six CDRs of the antibody "2.8.14" as disclosed herein).

Another aspect of the invention is an antibody specifically binding to minipig IgG, comprising a CDR1 of the heavy chain of SEQ ID NO: 11, a CDR2 of the heavy chain of SEQ ID NO: 12, and a CDR3 of the heavy chain of SEQ ID NO: 13, a CDR1 of the light chain of SEQ ID NO: 14, a CDR2 of the light chain of SEQ ID NO: 15, and a CDR3 of the light chain of SEQ ID NO: 16 (corresponding to the six CDRs of the antibody "1.2.6" as disclosed herein).

Another aspect of the invention is an antibody specifically binding to minipig IgG, comprising a CDR1 of the heavy chain of SEQ ID NO: 19, a CDR2 of the heavy chain of SEQ ID NO: 20, and a CDR3 of the heavy chain of SEQ ID NO: 21, a CDR1 of the light chain of SEQ ID NO: 22, a CDR2 of the light chain of SEQ ID NO: 23, and a CDR3 of the light chain of SEQ ID NO: 24 (corresponding to the six CDRs of the antibody "2.3.8" as disclosed herein).

Another aspect of the invention is an antibody specifically binding to minipig IgG, comprising a CDR1 of the heavy chain of SEQ ID NO: 27, a CDR2 of the heavy chain of SEQ ID NO: 28, and a CDR3 of the heavy chain of SEQ ID NO: 29, a CDR1 of the light chain of SEQ ID NO: 30, a CDR2 of the light chain of SEQ ID NO: 31, and a CDR3 of the light chain of SEQ ID NO: 32 (corresponding to the six CDRs of the antibody "2.11.16" as disclosed herein)

Another aspect of the invention is the antibody specifically binding to minipig IgG according to the invention for use in a method for determining the presence or absence of an anti-drug antibody (ADA) in a minipig sample.

The methods and antibodies of the invention allow reliable detection of ADAs and drug/ADA complexes in minipig samples, e.g. plasma, vitreous humor and aqueous humor. Antibodies of the invention exhibit no relevant cross-reactivity with IgG from human or mouse. Antibodies of the invention are particularly suitable to be applied in methods of the invention as they exhibit a low signal-to-noise ratio. The methods of the invention allow a reliable detection in presence of high drug doses, e.g. in vitreous humor samples. Thus, the methods are, e.g., advantageous for assessing ADAs formed in response to ophthalmic drugs.

DETAILED DESCRIPTION OF THE INVENTION

1. Definitions

Figure 1:
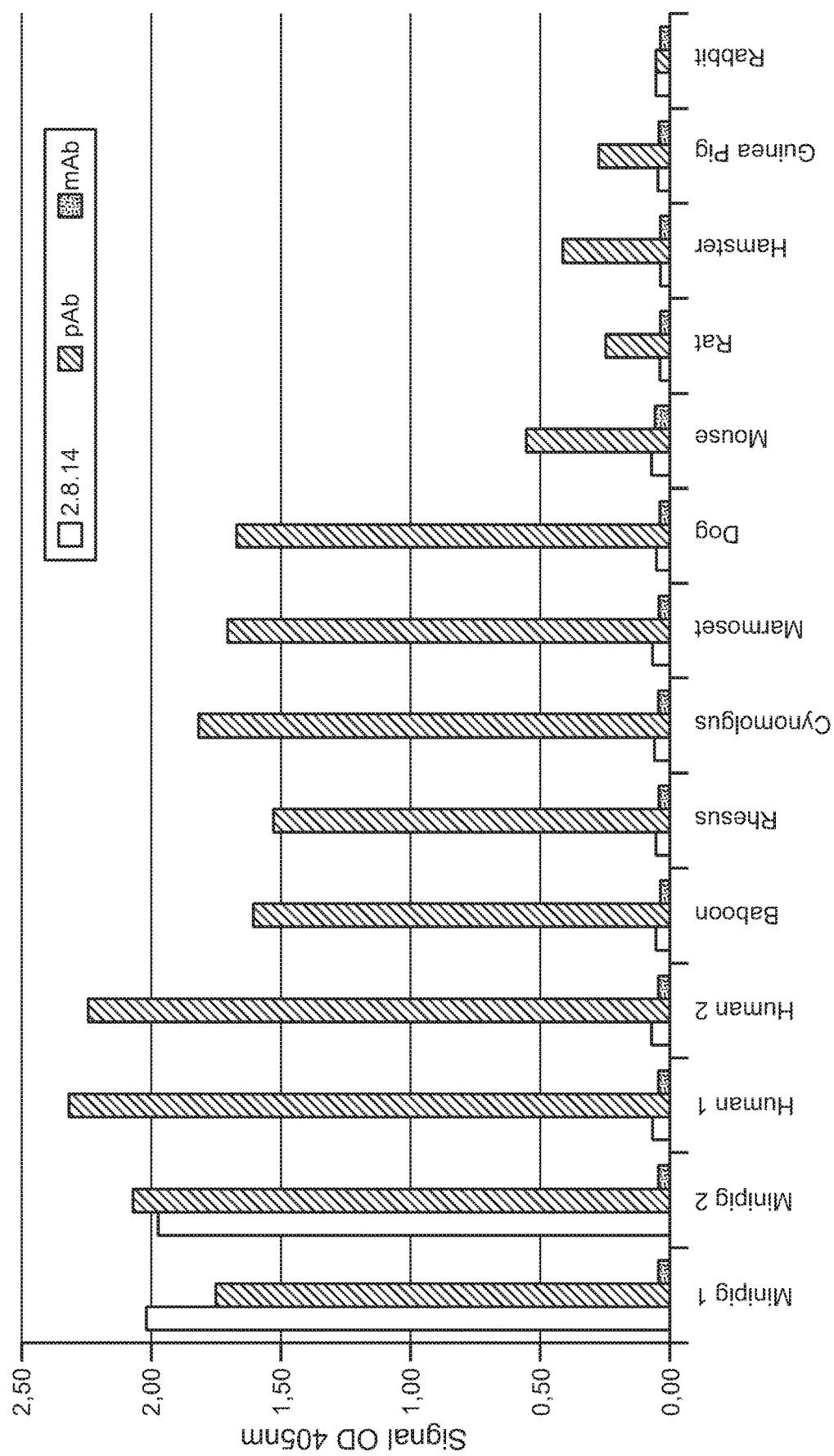
FIG. 1: Binding of monoclonal anti-minipig IgG 2.8.14, and commercially available HRP-conjugated polyclonal anti-pig IgG from Abd-Serotec (pAb) and digoxigenated monoclonal anti-pig IgG (mAb) to IgG from minipig, human, baboon, rhesus, cynomolgus, marmoset, dog, mouse, rat, hamster, guinea pig and rabbit (assessment as described in Example 3).

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present disclosure are generally performed according to conventional methods well known in the art. Generally, nomenclatures used in connection with the invention, and techniques of biochemistry, enzymology, molecular, and cellular biology, microbiology, genetics and protein and nucleic acid chemistry and hybridization described herein are those well-known and commonly used in the art.

Unless otherwise defined herein the term "comprising of" shall include the term "consisting of".

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The terms "anti-minipig IgG antibody" and "an antibody that binds to minipig IgG" refer to an antibody that is capable of binding minipig IgG with sufficient affinity such that the antibody is useful as a diagnostic agent in targeting minipig IgG. In certain embodiments, an antibody that binds to minipig IgG has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

An antibody is said to "specifically bind" to its target when the antibody has a Kd of 1 µM or less. Consequently, an antibody that does "not specifically bind" to its target is herein understood as having a Kd of more then 1 µM.

The term "drug" as used herein denotes a therapeutically active compound. The term "drug antibody" as used herein denotes an antibody which can be administered to an individual for the treatment of a disease, e.g. a therapeutic monoclonal antibody. Drug antibodies (therapeutic monoclonal antibodies) are being used widely for the treatment of various diseases such as oncological diseases (e.g. hematological and solid malignancies including non-Hodgkin's lymphoma, breast cancer, and colorectal cancer), immunological diseases, central nervous diseases, vascular diseases, or infectious diseases. Such antibodies are described, for example, by Levene, A. P., et al., Journal of the Royal Society of Medicine 98 (2005) 145-152. Such antibodies are, for instance, antibodies against CD20, CD22, HLA-DR, CD33, CD52, EGFR, G250, GD3, HER2, PSMA, CD56, VEGF, VEGF2, CEA, Lewis Y antigen, IL-6 receptor, or IGF-1 receptor. Therapeutic antibodies are also described by Groner, B., et al., Curr. Mol. Meth. 4 (2004) 539-547; Harris, M., Lancet Oncol. 5 (2004) 292-302.

"Anti-drug antibodies" or "ADA" as used herein denotes antibodies, which specifically bind to a drug, e.g. a drug antibody. ADA may be formed during antibody therapy as an immunogenic reaction of a patient (see Pan, Y., et al., FASEB J. 9 (1995) 43-49). In case the drug is a drug antibody, the ADA may specifically bind to any region of the drug antibody, like e.g. the variable domain, the constant domains, or the glycostructure of the drug antibody. In many cases however, ADA may bind to one or more of the complementary determining regions of the drug antibody.

The "variable domains" or "variable region" as used herein denotes each of the pair of light and heavy chains which is involved directly in binding the antibody to the antigen. The variable domain of a light chain is abbreviated as "VL" and the variable domain of a light chain is abbreviated as "VH". The variable domains of human light chains and heavy chains have the same general structure. Each variable domain comprises four framework (FR) regions, the sequences of which are widely conserved. The FR are connected by three "hypervariable regions" (or "complementarity determining regions", CDRs). CDRs on each chain are separated by such framework amino acids. Therefore, the light and heavy chains of an antibody comprise from N- to C-terminal direction the domains FR1, CDR1, FR2, CDR2, FR3, CDR3, and FR4. The FR adopt a β-sheet conformation and the CDRs may form loops connecting the β-sheet structure. The CDRs in each chain are held in their three-dimensional structure by the FR and form together with the CDRs from the other chain an "antigen binding site". Especially, CDR3 of the heavy chain is the region which contributes most to antigen binding. CDR and FR regions are determined according to the standard definition of Kabat, et al., Sequences of Proteins of Immunological Interest, 5th ed., Public Health Service, National Institutes of Health, Bethesda, Md. (1991).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

As used herein, a "Fab fragment" refers to an antibody fragment comprising a light chain fragment comprising a VL domain and a constant domain of a light chain (CL), and a VH domain and a first constant domain (CH1) of a heavy chain.

The term "Fc region" herein is used to define a C-terminal region of an immunoglobulin heavy chain that contains at least a portion of the constant region. The term includes native sequence Fc regions and variant Fc regions.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

The Complementarity Determining Regions (CDRs) indicated herein for the anti-minipig IgG antibodies are determined by the IMGT numbering system (Lefranc, M.-P. et al., Nucleic Acids Research, 27, 209-212 (1999)).

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity for the purposes of the alignment. Alignment for purposes of determining percent amino acid sequence identity can be achieved in various ways that are within the skill in the art, for instance, using publicly available computer software such as BLAST, BLAST-2, Clustal W, Megalign (DNASTAR) software or the FASTA program package. Those skilled in the art can determine appropriate parameters for aligning sequences, including any algorithms needed to achieve maximal alignment over the full length of the sequences being compared. For purposes herein, however, % amino acid sequence identity values are generated using the ggsearch program of the FASTA package version 36.3.8c or later with a BLOSUM50 comparison matrix. The FASTA program package was authored by W. R. Pearson and D. J. Lipman (1988), "Improved Tools for Biological Sequence Analysis", PNAS 85:2444-2448; W. R. Pearson (1996) "Effective protein sequence comparison" Meth. Enzymol. 266:227-258; and Pearson et. al. (1997) Genomics 46:24-36 and is publicly available from fasta.bioch.virginia.edu/fasta_www2/fasta_down.shtml. Alternatively, a public server accessible at fasta.bioch.virginia.edu/fasta_www2/index.cgi can be used to compare the sequences, using the ggsearch (global protein:protein) program and default options (BLOSUM50; open: −10; ext: −2; Ktup=2) to ensure a global, rather than local, alignment is performed. Percent amino acid identity is given in the output alignment header.

In one embodiment the antibody according to the invention is a monoclonal antibody. The terms "monoclonal antibody" or "monoclonal antibody composition" as used herein refer to a preparation of antibody molecules of a single amino acid composition.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term that an antibody exhibits "no relevant cross-reactivity with IgG from human" or "no relevant cross-reactivity with IgG from mouse" or equivalents thereof as used herein refers to an antibody does not specifically bind to a human IgG or mouse IgG, respectively, i.e. which exhibits a dissociation constant (Kd) of $10^{-7}$ mol/L or more from the respective antigen.

The term "minipig sample" includes any quantity of a substance isolated from a minipig. Such substances include, but are not limited to, whole blood, serum, or plasma from such an individual, which are the most widely used sources of sample in preclinical routine. Such substances also include vitreous humor or aqueous humor.

The term "support" or "solid phase" as used herein in connection with a method of the invention means a solid matter suitable to have IgG molecules immobilized thereon. Both terms may be used interchangeably. Supports include particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; cuvettes, tubes, or other spectrometer sample containers. The support may be a stationary component, such as a tube, strip, cuvette, or microtiter plate, or may be a non-stationary component, such as beads and microparticles.

Immunoassays are well known to the skilled artisan. Methods for carrying out such assays as well as practical applications and procedures are summarized in related textbooks. Examples of related textbooks are Tijssen, P., Preparation of enzyme-antibody or other enzyme-macromolecule conjugates, In: Practice and theory of enzyme immunoassays, Burdon, R. H. and v. Knippenberg, P. H. (eds.), Elsevier, Amsterdam (1990) pp. 221-278, and various volumes of Colowick, S. P. and Caplan, N. O. (eds.), "Methods in Enzymology", Academic Press, dealing with immunological detection methods, especially volumes 70, 73, 74, 84, 92, and 121.

The term "detectable label" as used herein refers to a substance capable of being detected by means known in the art. Detectable labels may be directly detectable, e.g. like chromogens (fluorescent or luminescent groups and dyes), or indirectly detectable, e.g. enzymes or haptens, such as digoxigenin. In one embodiment the detectable label is a hapten, and the detection is carried out using an enzyme-coupled hapten-specific antibody by visualizing the binding of the hapten-specific antibody to the hapten by assessing enzymatic activity in a color-change test.

2. Detailed Description of the Embodiments of the Invention

In one aspect, the invention provides a method for determining the presence or absence of anti-drug antibody (ADA) formed in response to a drug applied to a minipig, from a sample isolated from the minipig. The method is an immunoassay that allows detection of immunecomplexes comprising the drug and the ADA ("drug/ADA complexes") that are formed upon contacting the drug with the minipig sample. Drug/ADA complexes are bound by antibodies specifically binding to minipig IgG ("anti-minipig IgG antibodies"), and in turn the binding of the anti-minipig IgG antibodies to the drug/ADA complexes is detected and is indicative for the presence of ADA in the sample. This method allows detection of both, drug/ADA complexes that were already present in the minipig sample and non-complexed ADA from the initial sample.

Hence, in one aspect the invention relates to an in vitro method for determining the presence or absence of an anti-drug antibody (ADA) in a minipig sample, the method comprising:

a) contacting the sample with an excess amount of a drug to which the ADA binds to form drug/ADA complexes,
b) contacting the drug/ADA complexes with an antibody specifically binding minipig IgG, wherein the antibody specifically binding to minipig IgG does not bind to human IgG, and
c) determining the binding of the antibody specifically binding to minipig IgG to the drug/ADA complexes to determine whether ADA is present in the sample.

In one embodiment in step a) the drug is immobilized on a support.

In another aspect, the invention provides a method for determining the presence or absence of drug/ADA complexes in a minipig sample. The method is an immunoassay that allows direct detection of drug/ADA complexes from the minipig sample, which does not include a step of pre-incubating the minipig sample with the drug. Drug/ADA complexes from the sample are bound by antibodies specifically binding to the drug, and in turn the binding of the drug/ADA complexes to the antibody specifically binding to the drug is detected and is indicative for the presence of drug/ADA complexes in the sample.

Hence, in this aspect the invention relates to an in vitro method for determining the presence or absence of immune complexes comprising a drug and an antibody specifically binding to the drug (drug/ADA complexes) in a minipig sample, the method comprising:
 a) contacting the minipig sample with an immobilized antibody that specifically binds to the drug to immobilize the drug/ADA complexes present in the minipig sample,
 b) contacting the drug/ADA complexes with an antibody specifically binding minipig IgG, wherein the antibody specifically binding to minipig IgG does not bind to human IgG, and
 c) determining the binding of the antibody specifically binding to minipig IgG to the drug/ADA complexes to determine whether ADA is present in the sample.

Both methods of the invention are carried out in the indicated sequential order, i.e. step a) is followed by step b), which in turn is followed by step c). The following embodiments apply to both methods of the invention, i.e. the method for detecting the presence or absence of ADA in a minipig sample as well as the method for detecting the presence or absence of drug/ADA complexes in a minipig sample:

In one embodiment of the method of the invention the antibody specifically binding to minipig IgG does not specifically bind to human IgG. In one embodiment of the method of the invention the antibody specifically binding to minipig IgG does not specifically bind to mouse IgG. In one embodiment of the method of the invention the antibody specifically binding to minipig IgG does not specifically bind to human IgG and mouse IgG.

Thereby the sensitivity and reliability of the assay is improved as background variations caused e.g. by binding to a drug antibody of human or mouse species, may be minimized or even excluded.

In one embodiment of the method of the invention the antibody specifically binding to minipig IgG specifically binds to the Fc domain of minipig IgG.

In one embodiment of the method of the invention the antibody specifically binding to minipig IgG specifically binds to the Fab domain of minipig IgG.

In one embodiment of the method of the invention at least one antibody that specifically binds to the Fab domain of minipig IgG and at least one antibody that specifically binds to the Fc domain of minipig IgG are used in step b).

In one embodiment of the method of the invention, the drug used in step a) is immobilized on a support.

In one embodiment of the method of the invention the drug is a drug antibody (DA). In one embodiment the drug antibody is a human or humanized antibody. In one embodiment the drug antibody is an IgG antibody. In one embodiment the drug antibody is a human or humanized IgG antibody. In one embodiment the drug antibody is a Fab fragment.

In one embodiment of the method of the invention, wherein the drug antibody is a Fab fragment, step b) is carried out using a an antibody specifically binding to the Fab domain of minipig IgG.

In one embodiment of the method of the invention the method is a sandwich assay, wherein the drug/ADA complexes are contacted with an antibody specifically binding to human IgG, wherein the antibody specifically binding to human IgG is immobilized on a support, thereby immobilizing the drug/ADA complexes on the support, and wherein the immobilized drug/ADA complexes are subsequently contacted with the antibody specifically binding to minipig IgG according to step b) of the methods of the invention.

In one embodiment of the method of the invention the antibody specifically binding to minipig IgG is conjugated to a detectable label. In one embodiment the detectable label is a hapten. In one embodiment the detectable label is digoxigenin.

The invention also relates to antibodies specifically binding to minipig IgG. Antibodies of the invention specifically bind either to the Fc or Fab portion of minipig IgG and exhibit no relevant cross-reactivity with IgG from human and mouse. Antibodies of the invention are particularly useful in a method of the invention for determining the presence or absence of an anti-drug antibody (ADA) in a minipig sample.

In one aspect the invention relates to an antibody specifically binding to minipig IgG comprising a CDR1 of the heavy chain of SEQ ID NO: 3, a CDR2 of the heavy chain of SEQ ID NO: 4, and a CDR3 of the heavy chain of SEQ ID NO: 5, a CDR1 of the light chain of SEQ ID NO: 6, a CDR2 of the light chain of SEQ ID NO: 7, and a CDR3 of the light chain of SEQ ID NO: 8. In one embodiment said antibody comprises a VH sequence having at least 95% sequence identity to the amino acid sequence of SEQ ID NO: 1; and a VL sequence having at least 95% sequence identity to the amino acid sequence of SEQ ID NO: 2. In one embodiment said antibody comprises a VH sequence of SEQ ID NO: 1 and a VL sequence of SEQ ID NO: 2. The CDRs as well as VH and VL amino acid sequences correspond to the CDRs and variable domains of the antibody "2.8.14" as disclosed herein, which specifically binds to the Fc domain of minipig IgG.

In one aspect the invention relates to an antibody specifically binding to minipig IgG comprising a CDR1 of the heavy chain of SEQ ID NO: 11, a CDR2 of the heavy chain of SEQ ID NO: 12, and a CDR3 of the heavy chain of SEQ ID NO: 13, a CDR1 of the light chain of SEQ ID NO: 14, a CDR2 of the light chain of SEQ ID NO: 15, and a CDR3 of the light chain of SEQ ID NO: 16. In one embodiment said antibody comprises a VH sequence having at least 95% sequence identity to the amino acid sequence of SEQ ID NO: 9; and a VL sequence having at least 95% sequence identity to the amino acid sequence of SEQ ID NO: 10. In one embodiment said antibody comprises a VH sequence of SEQ ID NO: 9 and a VL sequence of SEQ ID NO: 10.

The CDRs as well as VH and VL amino acid sequences correspond to the CDRs and variable domains of the antibody "1.2.6" as disclosed herein, which specifically binds to the Fab domain of minipig IgG.

In one aspect the invention relates to an antibody specifically binding to minipig IgG comprising a CDR1 of the heavy chain of SEQ ID NO: 19, a CDR2 of the heavy chain of SEQ ID NO: 20, and a CDR3 of the heavy chain of SEQ ID NO: 21, a CDR1 of the light chain of SEQ ID NO: 22, a CDR2 of the light chain of SEQ ID NO: 23, and a CDR3 of the light chain of SEQ ID NO: 24. In one embodiment said antibody comprises a VH sequence having at least 95% sequence identity to the amino acid sequence of SEQ ID NO: 17; and a VL sequence having at least 95% sequence identity to the amino acid sequence of SEQ ID NO: 18. In one embodiment said antibody comprises a VH sequence of SEQ ID NO: 17 and a VL sequence of SEQ ID NO: 18. The CDRs as well as VH and VL amino acid sequences correspond to the CDRs and variable domains of the antibody "2.3.8" as disclosed herein, which specifically binds to the Fab domain of minipig IgG.

In one aspect the invention relates to an antibody specifically binding to minipig IgG comprising a CDR1 of the heavy chain of SEQ ID NO: 27, a CDR2 of the heavy chain of SEQ ID NO: 28, and a CDR3 of the heavy chain of SEQ ID NO: 29, a CDR1 of the light chain of SEQ ID NO: 30, a CDR2 of the light chain of SEQ ID NO: 31, and a CDR3 of the light chain of SEQ ID NO: 32. In one embodiment said antibody comprises a VH sequence having at least 95% sequence identity to the amino acid sequence of SEQ ID NO: 25; and a VL sequence having at least 95% sequence identity to the amino acid sequence of SEQ ID NO: 26. In one embodiment said antibody comprises a VH sequence of SEQ ID NO: 25 and a VL sequence of SEQ ID NO: 26. The CDRs as well as VH and VL amino acid sequences correspond to the CDRs and variable domains of the antibody "2.11.16" as disclosed herein, which specifically binds to the Fab domain of minipig IgG.

Another aspect of the invention is the use of the antibodies of the invention in a method for determining the presence or absence of an anti-drug antibody (ADA) in a minipig sample. In one embodiment the antibodies of the invention are used in a method of the invention.

3. Specific Embodiments of the Invention

In the following specific embodiments of the invention are listed.

1. An in vitro method for determining the presence or absence of an anti-drug antibody (ADA) in a minipig sample, the method comprising:
   a) contacting the sample with an excess amount of a drug to which the ADA binds to form drug/ADA complexes,
   b) contacting the drug/ADA complexes with an antibody specifically binding minipig IgG, wherein the antibody specifically binding to minipig IgG does not bind to human IgG, and
   c) determining the binding of the antibody specifically binding to minipig IgG to the drug/ADA complexes to determine whether ADA is present in the sample.
2. The method of embodiment 1, wherein in step a) the drug is immobilized on a support.
3. An in vitro method for determining the presence or absence of immune complexes comprising a drug and an antibody specifically binding to the drug (drug/ADA complexes) in a minipig sample, the method comprising:
   a) contacting the minipig sample with an immobilized antibody that specifically binds to the drug to immobilize the drug/ADA complexes present in the minipig sample,
   b) contacting the drug/ADA complexes with an antibody specifically binding minipig IgG, wherein the antibody specifically binding to minipig IgG does not bind to human IgG, and
   c) determining the binding of the antibody specifically binding to minipig IgG to the drug/ADA complexes to determine whether ADA is present in the sample.
4. The method of one of embodiments 1 to 3, wherein the antibody specifically binding to minipig IgG does not specifically bind to human IgG.
5. The method of one of embodiments 1 to 4, wherein the antibody specifically binding to minipig IgG does not specifically bind to mouse IgG.
6. The method of one of embodiments 1 to 5, wherein the antibody specifically binding to minipig IgG specifically binds to the Fc domain of minipig IgG.
7. The method of embodiment 6, wherein the antibody specifically binding to the Fc domain of minipig IgG comprises a CDR1 of the heavy chain of SEQ ID NO: 3, a CDR2 of the heavy chain of SEQ ID NO: 4, and a CDR3 of the heavy chain of SEQ ID NO: 5, a CDR1 of the light chain of SEQ ID NO: 6, a CDR2 of the light chain of SEQ ID NO: 7, and a CDR3 of the light chain of SEQ ID NO: 8 (corresponding to the six CDRs of the antibody "2.8.14" as disclosed herein).
8. The method of embodiment 6 or 7, wherein the antibody specifically binding to the Fc domain of minipig IgG comprises a VH sequence of SEQ ID NO: 1 and a VL sequence of SEQ ID NO: 2 (corresponding to the variable domains of the antibody "2.8.14" as disclosed herein).
9. The method of one of embodiments 1 to 5, wherein the antibody specifically binding to minipig IgG specifically binds to the Fab domain of minipig IgG.
10. The method of embodiment 9, wherein the antibody specifically binding to the Fab domain of minipig IgG comprises a CDR1 of the heavy chain of SEQ ID NO: 11, a CDR2 of the heavy chain of SEQ ID NO: 12, and a CDR3 of the heavy chain of SEQ ID NO: 13, a CDR1 of the light chain of SEQ ID NO: 14, a CDR2 of the light chain of SEQ ID NO: 15, and a CDR3 of the light chain of SEQ ID NO: 16 (corresponding to the six CDRs of the antibody "1.2.6" as disclosed herein).
11. The method of embodiment 9 or 10, wherein the antibody specifically binding to the Fab domain of minipig IgG comprises a VH sequence of SEQ ID NO: 9 and a VL sequence of SEQ ID NO: 10 (corresponding to the variable domains of the antibody "1.2.6" as disclosed herein).
12. The method of embodiment 9, wherein the antibody specifically binding to the Fab domain of minipig IgG comprises a CDR1 of the heavy chain of SEQ ID NO: 19, a CDR2 of the heavy chain of SEQ ID NO: 20, and a CDR3 of the heavy chain of SEQ ID NO: 21, a CDR1 of the light chain of SEQ ID NO: 22, a CDR2 of the light chain of SEQ ID NO: 23, and a CDR3 of the light chain of SEQ ID NO: 24 (corresponding to the six CDRs of the antibody "2.3.8" as disclosed herein).
13. The method of embodiment 9 or 12, wherein the antibody specifically binding to the Fab domain of minipig IgG comprises a VH sequence of SEQ ID NO: 17 and a VL sequence of SEQ ID NO: 18 (corresponding to the variable domains of the antibody "2.3.8" as disclosed herein).
14. The method of embodiment 9, wherein the antibody specifically binding to the Fab domain of minipig IgG comprises a CDR1 of the heavy chain of SEQ ID NO: 27, a CDR2 of the heavy chain of SEQ ID NO: 28, and a CDR3 of the heavy chain of SEQ ID NO: 29, a CDR1 of the light chain of SEQ ID NO: 30, a CDR2 of the light chain of SEQ ID NO: 31, and a CDR3 of the light chain of SEQ ID NO: 32 (corresponding to the six CDRs of the antibody "2.11.16" as disclosed herein).
15. The method of embodiment 9 or 14, wherein the antibody specifically binding to the Fab domain of minipig IgG comprises a VH sequence of SEQ ID NO: 25 and a VL sequence of SEQ ID NO: 26 (corresponding to the variable domains of the antibody "2.11.16" as disclosed herein).
16. The method of one of the preceding embodiments, wherein at least one antibody that specifically binds to the Fab domain of minipig IgG and at least one antibody that specifically binds to the Fc domain of minipig IgG are used in step b).
17. The method of one of embodiments 1 to 16, wherein the drug is a drug antibody (DA).
18. The method of embodiment 17, wherein the drug antibody is a human or humanized antibody.
19. The method of embodiment 17 or 18, wherein the drug antibody is an IgG antibody.
20. The method of one of embodiments 17 to 19, wherein the drug antibody is a Fab fragment.
21. The method of embodiment 20, wherein an antibody specifically binding to the Fab domain of minipig IgG is used in step b).
22. The method of embodiment 21, wherein the antibody specifically binding to the Fab domain of minipig IgG is selected from the antibodies defined in embodiments 7 to 13.
23. The method of one of embodiments 17 to 22, wherein the method is a sandwich assay, wherein in step a) the drug/ADA complexes are contacted with an antibody specifically binding to human IgG, wherein the antibody specifically binding to human IgG is immobilized on a support, thereby immobilizing the drug/ADA complexes on the support, and
    wherein the immobilized drug/ADA complexes are subsequently contacted with the antibody specifically binding to minipig IgG according to step b).
24. The method of one of embodiments 1 to 23, wherein the antibody specifically binding to minipig IgG is conjugated to a detectable label.
25. The method of embodiment 24, wherein the detectable label is digoxigenin.
26. An antibody specifically binding to minipig IgG, comprising a CDR1 of the heavy chain of SEQ ID NO: 3, a CDR2 of the heavy chain of SEQ ID NO: 4, and a CDR3 of the heavy chain of SEQ ID NO: 5, a CDR1 of the light chain of SEQ ID NO: 6, a CDR2 of the light chain of SEQ ID NO: 7, and a CDR3 of the light chain of SEQ ID NO: 8 (corresponding to the six CDRs of the antibody "2.8.14" as disclosed herein).
27. The antibody according to embodiment 26, comprising a VH sequence having at least 95% sequence identity to the amino acid sequence of SEQ ID NO: 1; and a VL sequence having at least 95% sequence identity to the amino acid sequence of SEQ ID NO: 2.
28. The antibody according to embodiment 26 or 27, comprising a VH sequence of SEQ ID NO: 1 and a VL sequence of SEQ ID NO: 2 (corresponding to the variable domains of the antibody "2.8.14" as disclosed herein).
29. An antibody specifically binding to minipig IgG comprising a CDR1 of the heavy chain of SEQ ID NO: 11, a CDR2 of the heavy chain of SEQ ID NO: 12, and a CDR3 of the heavy chain of SEQ ID NO: 13, a CDR1 of the light chain of SEQ ID NO: 14, a CDR2 of the light chain of SEQ ID NO: 15, and a CDR3 of the light chain of SEQ ID NO: 16 (corresponding to the six CDRs of the antibody "1.2.6" as disclosed herein).
30. The antibody of embodiment 29 comprising a VH sequence having at least 95% sequence identity to the amino acid sequence of SEQ ID NO: 9; and a VL sequence having at least 95% sequence identity to the amino acid sequence of SEQ ID NO: 10.
31. The antibody of embodiment 29 comprising a VH sequence of SEQ ID NO: 9 and a VL sequence of SEQ ID NO: 10 (corresponding to the variable domains of the antibody "1.2.6" as disclosed herein).
32. An antibody specifically binding to minipig IgG comprising a CDR1 of the heavy chain of SEQ ID NO: 19, a CDR2 of the heavy chain of SEQ ID NO: 20, and a CDR3 of the heavy chain of SEQ ID NO: 21, a CDR1 of the light chain of SEQ ID NO: 22, a CDR2 of the light chain of SEQ ID NO: 23, and a CDR3 of the light chain of SEQ ID NO: 24 (corresponding to the six CDRs of the antibody "2.3.8" as disclosed herein).
33. The antibody of embodiment 32 comprising a VH sequence having at least 95% sequence identity to the amino acid sequence of SEQ ID NO: 17; and a VL sequence having at least 95% sequence identity to the amino acid sequence of SEQ ID NO: 18.
34. The antibody of embodiment 32 comprising a VH sequence of SEQ ID NO: 17 and a VL sequence of SEQ ID NO: 18 (corresponding to the variable domains of the antibody "2.3.8" as disclosed herein).
35. An antibody specifically binding to minipig IgG comprising a CDR1 of the heavy chain of SEQ ID NO: 27, a CDR2 of the heavy chain of SEQ ID NO: 28, and a CDR3 of the heavy chain of SEQ ID NO: 29, a CDR1 of the light chain of SEQ ID NO: 30, a CDR2 of the light chain of SEQ ID NO: 31, and a CDR3 of the light chain of SEQ ID NO: 32 (corresponding to the six CDRs of the antibody "2.11.16" as disclosed herein).
36. The antibody of embodiment 35 comprising a VH sequence having at least 95% sequence identity to the amino acid sequence of SEQ ID NO: 25; and a VL sequence having at least 95% sequence identity to the amino acid sequence of SEQ ID NO: 26.
37. The antibody of embodiment 35 comprising a VH sequence of SEQ ID NO: 25 and a VL sequence of SEQ ID NO: 26 (corresponding to the variable domains of the antibody "2.11.16" as disclosed herein).
38. The antibody of one of embodiments 26 to 37 for use in a method for determining the presence or absence of an anti-drug antibody (ADA) in a minipig sample.
39. The antibody of one of embodiments 26 to 37 for use in a method of one of embodiments 1 to 25.

| DESCRIPTION OF THE AMINO ACID SEQUENCES | | |
| --- | --- | --- |
| SEQ ID NO: 1 | anti-minipig IgG clone "2.8.14" | VH |
| SEQ ID NO: 2 | anti-minipig IgG clone "2.8.14" | VL |
| SEQ ID NO: 3 | anti-minipig IgG clone "2.8.14" | VH CDR1 (IMGT) |
| SEQ ID NO: 4 | anti-minipig IgG clone "2.8.14" | VH CDR2 (IMGT) |
| SEQ ID NO: 5 | anti-minipig IgG clone "2.8.14" | VH CDR3 (IMGT) |
| SEQ ID NO: 6 | anti-minipig IgG clone "2.8.14" | VL CDR1 (IMGT) |
| SEQ ID NO: 7 | anti-minipig IgG clone "2.8.14" | VL CDR2 (IMGT) |

-continued

| DESCRIPTION OF THE AMINO ACID SEQUENCES | | |
|---|---|---|
| SEQ ID NO: 8 | anti-minipig IgG clone "2.8.14" | VL CDR3 (IMGT) |
| SEQ ID NO: 9 | anti-minipig IgG clone "1.2.6" | VH |
| SEQ ID NO: 10 | anti-minipig IgG clone "1.2.6" | VL |
| SEQ ID NO: 11 | anti-minipig IgG clone "1.2.6" | VH CDR1 (IMGT) |
| SEQ ID NO: 12 | anti-minipig IgG clone "1.2.6" | VH CDR2 (IMGT) |
| SEQ ID NO: 13 | anti-minipig IgG clone "1.2.6" | VH CDR3 (IMGT) |
| SEQ ID NO: 14 | anti-minipig IgG clone "1.2.6" | VL CDR1 (IMGT) |
| SEQ ID NO: 15 | anti-minipig IgG clone "1.2.6" | VL CDR2 (IMGT) |
| SEQ ID NO: 16 | anti-minipig IgG clone "1.2.6" | VL CDR3 (IMGT) |
| SEQ ID NO: 17 | anti-minipig IgG clone "2.3.8" | VH |
| SEQ ID NO: 18 | anti-minipig IgG clone "2.3.8" | VL |
| SEQ ID NO: 19 | anti-minipig IgG clone "2.3.8" | VH CDR1 (IMGT) |
| SEQ ID NO: 20 | anti-minipig IgG clone "2.3.8" | VH CDR2 (IMGT) |
| SEQ ID NO: 21 | anti-minipig IgG clone "2.3.8" | VH CDR3 (IMGT) |
| SEQ ID NO: 22 | anti-minipig IgG clone "2.3.8" | VL CDR1 (IMGT) |
| SEQ ID NO: 23 | anti-minipig IgG clone "2.3.8" | VL CDR2 (IMGT) |
| SEQ ID NO: 24 | anti-minipig IgG clone "2.3.8" | VL CDR3 (IMGT) |
| SEQ ID NO: 25 | anti-minipig IgG clone "2.11.16" | VH |
| SEQ ID NO: 26 | anti-minipig IgG clone "2.11.16" | VL |
| SEQ ID NO: 27 | anti-minipig IgG clone "2.11.16" | VH CDR1 (IMGT) |
| SEQ ID NO: 28 | anti-minipig IgG clone "2.11.16" | VH CDR2 (IMGT) |
| SEQ ID NO: 29 | anti-minipig IgG clone "2.11.16" | VH CDR3 (IMGT) |
| SEQ ID NO: 30 | anti-minipig IgG clone "2.11.16" | VL CDR1 (IMGT) |
| SEQ ID NO: 31 | anti-minipig IgG clone "2.11.16" | VL CDR2 (IMGT) |
| SEQ ID NO: 32 | anti-minipig IgG clone "2.11.16" | VL CDR3 (IMGT) |

EXAMPLES

The following examples are provided to aid the understanding of the present invention, the true scope of which is set forth in the appended claims. It is understood that modifications can be made in the procedures set forth without departing from the spirit of the invention.

Example 1

Generation of Minipig IgG

Serum from minipig was delipidated with Aerosil® 380 and precipitated with ammonium sulfate (ad 2.0 M). The pellet was homogenized in phosphate buffer and dialyzed against phosphate buffer, pH 7.0. The mixture was separated by DEAE ion exchange chromatography at pH 7.0 and the IgG in the flow through was concentrated and purified by gel filtration.

Example 2

Generation of Monoclonal Anti-Minipig IgG Antibodies

Anti-minipig antibodies were generated by immunization of mice with minipig IgG derived from minipig serum and subsequent hybridoma selection. Screening of appropriate clones was carried out in presence of human IgG to select the antibodies most potent for the intended application for detecting ADAs against human or humanized IgG drug antibodies.

a) Immunization of Mice

Female BALB/c or NMRI mice, respectively, were primarily immunized intraperitoneally with 90 µg of minipig IgG mixed with CFA (Complete Freund's Adjuvant). Two further intraperitoneal immunizations with 90 µg minipig IgG formulated with IFA (Incomplete Freund's Adjuvant) followed 6 and 10 weeks after the primary immunization. Subsequently, one intraperitoneal boost immunization with 50 µg minipig IgG and one intravenous boost immunization with 25 µg minipig IgG formulated in PBS buffer solution were performed three and two days, respectively, before the animals were sacrificed and the splenocytes were used for the generation of hybridoma as described below.

b) Fusion and Cloning

Fusion of the spleen cells of the mice immunized according to a) with myeloma cells was performed by standard procedures using polyethylene glycol. Briefly, approx. $1 \times 10^8$ splenocytes were mixed with approx. $2 \times 10^7$ myeloma cells (P3x63-Ag8.653) in RPMI-1640 and centrifuged (10 min, 250×g). The cells were washed once with RPMI-1640 and centrifuged again. Thereafter, 1 ml of PEG (polyethylene glycol) was added dropwise to the cell pellet. After incubation for 1 min in a water bath at 37° C., 5 ml of RPMI-1640 were added dropwise to the cells. Subsequently the cell suspension was filled up to 30 ml with RPMI-1640. After centrifugation (10 min, 180×g), cells were resuspended in selection medium (RPMI-1640 supplemented with 10% FCS, 100 U/ml IL-6, 2 mM L-glutamine, 100 µM NEAA, 1 mM sodium pyruvate, 24 µM 2-mercaptoethanol, 1× azaserine/hypoxanthine (Sigma-Aldrich)). After 24 h of cultivation at 37° C. cells were plated into 96-well cell culture plates. After 10 days of cultivation, the primary cultures were assayed for production of minipig IgG specific antibodies as described below. Selected primary cultures were cloned by single cell sorting using a flow cytometer (FACSAria, BD Biosciences). Cell clones were grown in RPMI-1640 supplemented with 10% FCS, 50 U/ml IL-6, 2 mM L-glutamine, 100 µM NEAA, 1 mM sodium pyruvate and 24 µM 2-mercaptoethanol. The established monoclonal hybridoma cell lines were re-tested for specificity as described below.

c) Selection of Hybridoma Expressing Anti-Minipig Antibodies with No Relevant Cross-Reactivity with Human IgG Primary Screening For identification of hybridoma secreting anti-minipig antibodies Streptavidin pre-coated microtiter plates (MTPs) (MicroCoat, Bernried, Germany) were coated with 100 µl per well biotinylated minipig IgG (250 ng/ml in PBS/1.0% (w/v) BSA) for 1 h at room temperature (RT). Subsequently, the wells were washed 3 times with wash buffer (0.9% (w/v) NaCl/0.05% Tween® 20). Afterwards, 75 µL of hybridoma cell culture supernatant was added to each well and incubated for 1 h at RT. After washing 100 μL of a horseradish peroxidase-labeled F(ab')2 fragment of a polyclonal sheep anti-mouse Fcγ antibody was added for the detection of bound antibody and incubated for 1 h at RT. After washing 100 μL of ABTS® (Roche, Germany) were added to each well and extinction (OD) was measured at 405 and 492 nm [405/492] in a microtiter plate reader. This screening led to a selection of antibodies binding to minipig IgG.

Second Screening

In order to identify those anti-minipig antibodies that exhibit the lowest cross-reactivity to human IgG, the following competition assay was performed. MTPs pre-coated with recombinant streptavidin (MicroCoat) were coated with 100 μl per well biotinylated minipig IgG (250 ng/ml in PBS/1.0% BSA) as described above. Subsequently, coated plates were washed with 0.9% NaCl/0.05% Tween-20®. In the next step, a mixture of 37.5 μl of the anti-minipig antibody (hybridoma cell culture supernatant) and 37.5 μl polyclonal human IgG (at a final concentration of 40 mg/ml) was added to the wells. In a control experiment, a mixture of 37.5 μL of the respective anti-minipig antibody (hybridoma cell culture supernatant) and 37.5 μl buffer (PBS/1.0% BSA) was added to the wells. Plates were incubated for 1 h at RT. After washing with 0.9% NaCl/0.05% Tween-20®, 100 μl/well of a horseradish peroxidase-labeled F(ab')2 fragment of a polyclonal sheep anti-mouse Fcγ antibody (100 ng/ml) were added for the detection of bound sample antibody. After incubation for 1 h at RT plates were washed as described above. Finally, 100 μl/well of ABTS® (Roche Diagnostics GmbH) were added and extinction (OD) was measured at 405 and 492 nm [405/492]. Anti-minipig IgG antibodies showing the least reduction of signal in the presence of the polyclonal human IgG (compared to the buffer control) show the lowest cross-reactivity.

This screening approach led to a selection of antibodies binding well to minipig IgG as well as exhibiting no relevant cross reactivity to human IgG.

d) Identification of the Binding Region of the Generated Anti-Minipig Antibodies In order to identify the binding region of the anti-minipig antibodies, MTPs pre-coated with recombinant streptavidin (MicroCoat) were coated with 100 μl per well biotinylated minipig IgG (250 ng/ml in PBS/1.0% BSA), 100 μl per well biotinylated minipig Fab-fragment (250 ng/ml in PBS/1.0% BSA) or 100 μl per well biotinylated minipig IgG Fc-fragment (250 ng/ml in PBS/1.0% BSA), respectively. After washing of the coated MTPs with 0.9% NaCl/0.05% Tween-20®, 100 μL of the anti-minipig antibody (hybridoma cell culture supernatant; 1:2 diluted in PBS/1.0% BSA) was added to the wells. Plates were incubated for 1 h at RT. Subsequently, coated plates were washed with 0.9% NaCl/0.05% Tween-20®. After washing with 0.9% NaCl/0.05% Tween-20®, 100 μl/well of a horseradish peroxidase-labeled F(ab')$_2$ fragment of a polyclonal sheep anti-mouse Fcγ antibody (100 ng/ml) were added for the detection of bound antibody. After incubation for 1 h at RT plates were washed as described above. Finally, 100 μl/well of ABTS® (Roche Diagnostics GmbH) were added and extinction (OD) was measured at 405 and 492 nm [405/492].

To confirm the results of the ELISA described above, a competition ELISA has been performed. Briefly, MTPs pre-coated with recombinant streptavidin (MicroCoat) were coated with 100 μl per well biotinylated minipig IgG (250 ng/ml in PBS/1.0% BSA), 100 μl per well biotinylated minipig Fab-fragment (250 ng/ml in PBS/1.0% BSA) or 100 μl per well biotinylated minipig IgG Fc-fragment (250 ng/ml in PBS/1.0% BSA), respectively. Subsequently, coated plates were washed with 0.9% NaCl/0.05% Tween-20®. In the next step, a mixture of 50 μl of the anti-minipig antibody (hybridoma cell culture supernatant) and 50 μl polyclonal minipig Fab-fragment (at a final concentration of 5 μg/ml in PBS/1.0% BSA, preincubated at RT for 30 minutes) was added to the wells. In a control experiment, a mixture of 50 μL of the respective anti-minipig antibody (hybridoma cell culture supernatant) and 50 μl buffer (PBS/1.0% BSA) was added to the wells. Plates were incubated for 1 h at RT. After washing with 0.9% NaCl/0.05% Tween-20®, 100 μl/well of a horseradish peroxidase-labeled F(ab')$_2$ fragment of a polyclonal sheep anti-mouse Fcγ antibody (100 ng/ml) were added for the detection of bound sample antibody. After incubation for 1 h at RT plates were washed as described above. Finally, 100 μl/well of ABTS® (Roche Diagnostics GmbH) were added and extinction (OD) was measured at 405 and 492 nm [405/492].

This ELISA screening approach led to the identification of antibodies binding either to the minipig Fab- or Fc fragment.

The following clones (Table 1) were selected as suitable candidates.

TABLE 1 anti-minipig IgG clones

| Clone | IgG class and subclass | Immunogen | Reactivity |
|---|---|---|---|
| 2.8.14 | IgG1, kappa | minipig IgG | minipig IgG, Fc fragment |
| 1.2.6 | IgG1, kappa | minipig IgG | minipig IgG, Fab fragment |
| 2.3.8 | IgG1, kappa | minipig IgG | minipig IgG, Fab fragment |
| 2.11.16 | IgG1, kappa | minipig IgG | minipig IgG, Fab fragment | e) Production of Immunoglobulin

The generated monoclonal hybridoma cell lines were inoculated at initial cell densities of $1.0 \times 10^5$ to $2.2 \times 10^5$ cells per mL in Hybridoma-SFM medium (Gibco) supplemented with 5% FCS, 50 U/ml IL-6, 50 μM β-mercaptoethanol and 20 μM ethanolamine. The cells were expanded in a spinner flask for a period of 7 to 14 days. Subsequently, cell culture supernatants were harvested and antibodies were purified from supernatants according to standard protein chemical methods (see, e.g. Bruck, C., et al., Methods Enzymol. 121 (1986) 587-596).

Example 3

Cross-Reactivity of Generated Monoclonal Anti-Minipig IgG Antibody with IgG from Other Species The cross-reactivity of anti-minipig IgG antibody 2.8.14 as generated in example 2 was assessed and compared to two commercially available anti-minipig IgG antibodies, an HRP-conjugated goat polyclonal anti-pig IgG antibody (AbD-Serotec, Cat. AAI41P) and a mouse monoclonal anti-pig IgG antibody (AbD-Serotec, clone K139 3C8, Cat. MCA635GA), which was digoxigenated in-house. For clarification it is noted that as minipig is a class of pig, anti-pig antibodies are, of course, reactive with minipig antigens, i.e. the anti-pig IgG antibodies specifically bind to minipig-IgG. The following antibodies were compared:

digoxigenated anti-minipig IgG antibody "2.8.14"
HRP-conjugated polyclonal anti-pig IgG from Abd-Serotec as indicated above "pAb"
digoxigenated monoclonal anti-pig IgG "mAb"

Cross-reactivity was assessed in an immunoassay. In brief, serum or plasma from 12 different species were bound as a 5% matrix-concentrated dilution in an alkaline NaHCO$_3$- buffer to a NUNC Maxisorp plate. Two human samples and two minipig samples were used in addition to samples from baboon, rhesus, cynomolgus, marmoset, dog, mouse, rat, hamster, guinea pig, and rabbit. Plates were incubated with the three tested anti-minipig IgG antibodies at 2 μg/ml, which were either digoxigenated or conjugated to horse radish peroxidase (HRP) as indicated. Incubation with digoxigenated anti-minipig IgG was followed by an incubation with a polycolonal HRP-conjugated anti-digoxigenin Fab fragment (Roche Diagnostics, Cat. 11633716001). Detection was done by colour-change assessment using ABTS® substrate and detecting the signal at 405 nm (reference wavelength: 490 nm ([405/490] nm)) using a standard ELISA reader.

Results are shown in FIG. 1. The tested commercially available polyclonal antibody significantly cross-reacts with IgG from numerous species. The tested commercially available monoclonal antibody did not show significant binding to any none of the tested species, including minipig, in this assay.

Monoclonal antibody 2.8.14 according to the invention did not show cross-reactivity towards IgG from any one of the tested species other than minipig in this assay.

Example 4

Cross-Reactivity of Generated Monoclonal Anti-Minipig IgG Antibody with Human IgG Drug Antibodies The cross-reactivity of anti-minipig IgG antibodies 2.8.14 and 2.3.8 as generated in example 2 with several human IgG drug antibodies was assessed in an immunoassay and compared to a commercially available polyclonal anti-minipig IgG antibody ("pAb", as described in Example 3).

The test was run using a total of 13 different drug antibodies of human IgG isotype, the drugs being either full length IgG of a wild type antibody domain arrangement (indicated "h-IgG"), full length IgG CrossMabs (comprising a domain exchange as described in Klein et al. [MAbs. 2012 November-December; 4(6):653-63]; indicated "XMab"), or Fab fragments (indicated "h-Fab"). Minipig IgG (in-house preparation from minipig serum) was used as a positive control. For drugs 3, 5, 7 and 8, which are full length IgGs, fragments of the antibodies were tested as well as indicated in FIG. 2.

For detection of cross-reactivity towards anti-drug antibodies, the positive control and the drug antibodies were bound to a Maxisorp plate and detected using digoxigenated monoclonal antibodies 2.8.14, and 2.3.8 followed by incubation with an HRP-conjugated anti-digoxigenin antibody as well as HRP-conjugated polyclonal anti-pig IgG from Abd-Serotec ("pAb", as described in Example 3). Detection was done by colour-change assessment using ABTS® substrate and detecting the signal at 405 nm (reference wavelength: 490 nm ([405/490] nm)) using a standard ELISA reader.

Figure 2:
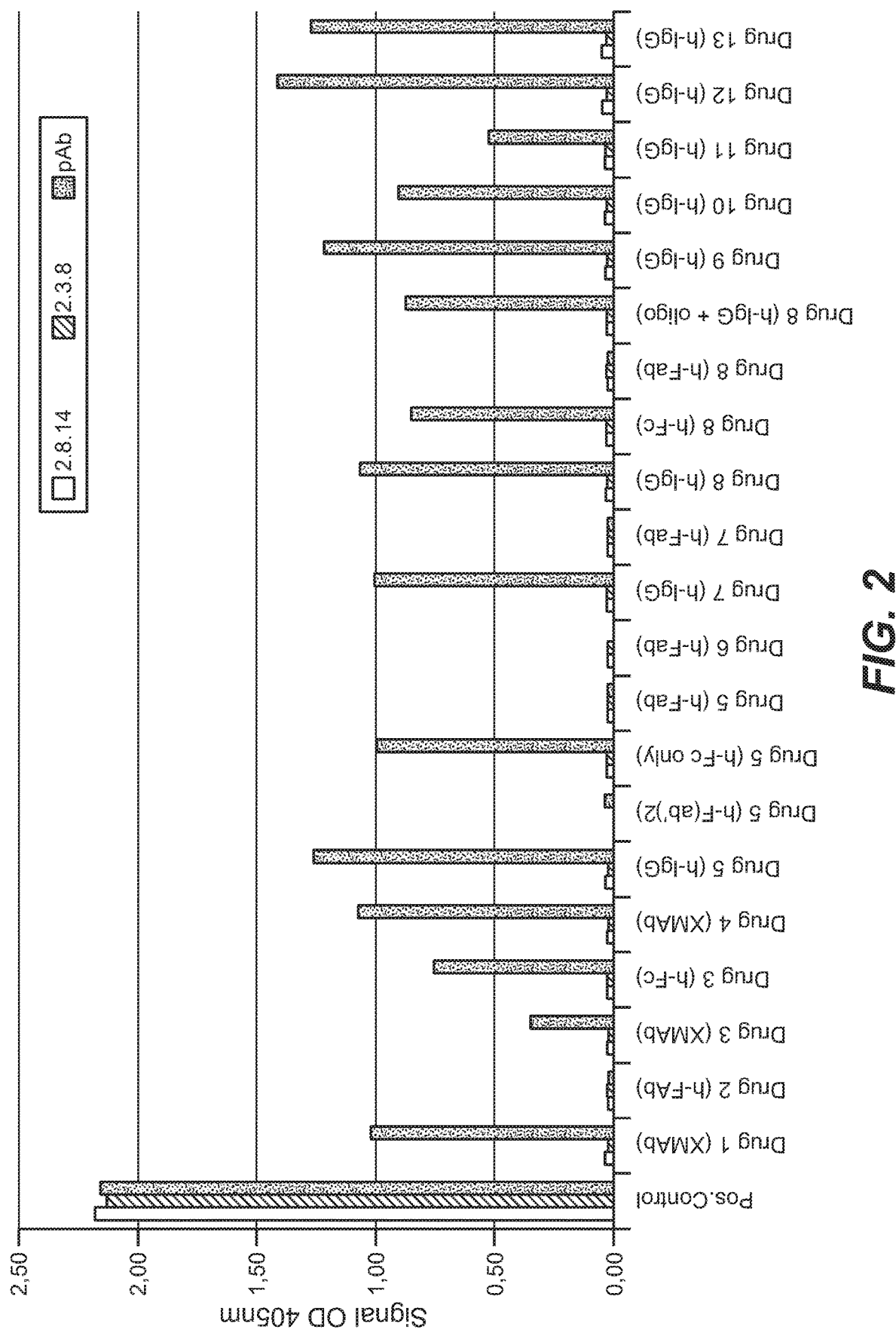
FIG. 2: Binding of monoclonal anti-minipig IgG 2.8.14 and 2.3.8, and commercially available polyclonal anti-pig IgG antibody to different drug antibodies of human IgG1 class (assessment as described in Example 4).

Results are shown in FIG. 2. Monoclonal antibodies 2.8.14 and 2.3.8 according to the invention did not show cross-reactivity with the tested drug antibodies or their fragments. The tested commercially available polyclonal anti-pig antibody significantly cross-reacts with all the full length IgG drug antibodies, and their Fc fragments, where tested.

Example 5

Applicability of Generated Monoclonal Anti-Minipig IgG Antibodies vs. Commercially Available Anti-Pig IgG Antibodies in a Method of the Invention for Detecting Drug/ADA Complexes in a Minipig Sample (without Pre-Incubation with Drug)

In order to assess the applicability of different anti-minipig IgG antibodies in a method of the invention for detection of in vivo formed drug/ADA complexes from a minipig sample several commercially available antibodies were compared to antibodies of the invention. The following antibodies were used:

monoclonal anti-pig antibody MAb<Sw-IgG>M-F007-1241-IgG-Dig (BD Pharmingen, Cat. 552554) ("mAb1")

monoclonal anti-pig antibody MAb<Sw-IgG>M-K139-3E1-IgG (AbD Serotec, Cat. MCA633GA) ("mAb2")

monoclonal anti-pig antibody MAb<Sw-IgG>M-K139-3C8-IgG (AbD Serotec, Cat. MCA633GA) ("mAb3")

polycolonal anti-pig antibody PAb<Pig-IgG-Fc>Rabbit-IgG-HRP (Rockland, Cat. 614-4303) ("pAb1")

polycolonal anti-pig antibody PAb<Pig-IgG-Fc>Goat-IgG-HRP (Bethyl (Biomol), Cat. A100-104P) ("pAb2")

polycolonal anti-pig antibody PAb<Pig-IgG-Fc>Goat-IgG-HRP, (AbD-Serotec, Cat. AAI41P) ("pAb3")

monoclonal anti-minipig IgG antibody 2.8.14 monoclonal anti-minipig IgG antibody 2.3.8 monoclonal anti-minipig IgG antibody 2.11.16

For detection of in vivo formed drug/ADA complexes from a minipig sample, the following assay (according to the invention) was used:

Biotinylated anti-human IgG-Fab (kappa) monoclonal antibody MAb<h-IgG-kappa>M-1.7.10-Fab' (Roche, as disclosed in WO 2012/022682) was bound to the wells of a Streptavidin-coated microtiter plate (SA-MTP) in the first step. Excess of unbound Fab'—fragment was removed by washing.

In order to mimic drug/ADA complexes human IgG/swine IgG conjugates were prepared. Therefore, polyclonal human IgG (purified from human serum) was chemically conjugated with polyclonal swine IgG (purified from pig serum). The so-derived human IgG/swine IgG conjugates were spiked in low, medium and high concentration in 2% minipig pool plasma and used as positive controls (wherein "LPC" refers to a low concentration, "MPC" to a medium concentration and "HPC" to a high concentration positive control). Minipig pool plasma (not spiked with human IgG/swine IgG conjugates) was used as a negative control.

Consequently, the controls were added to and incubated in the wells. After washing away unbound substances the human IgG/swine IgG conjugates (mimicking drig/ADA complexes) were detected with the indicated digoxigenylated anti-minipig antibody followed by an incubation with a horse-radish peroxidase labeled anti-digoxigenin antibody. The antibody-enzyme conjugate catalyzes the color reaction of the ABTS® substrate. The signal was measured by standard ELISA reader at 405 nm wavelength (reference wavelength: 490 nm ([405/490] nm)). Absorbance values of each sample were determined in duplicates.

Figure 3:
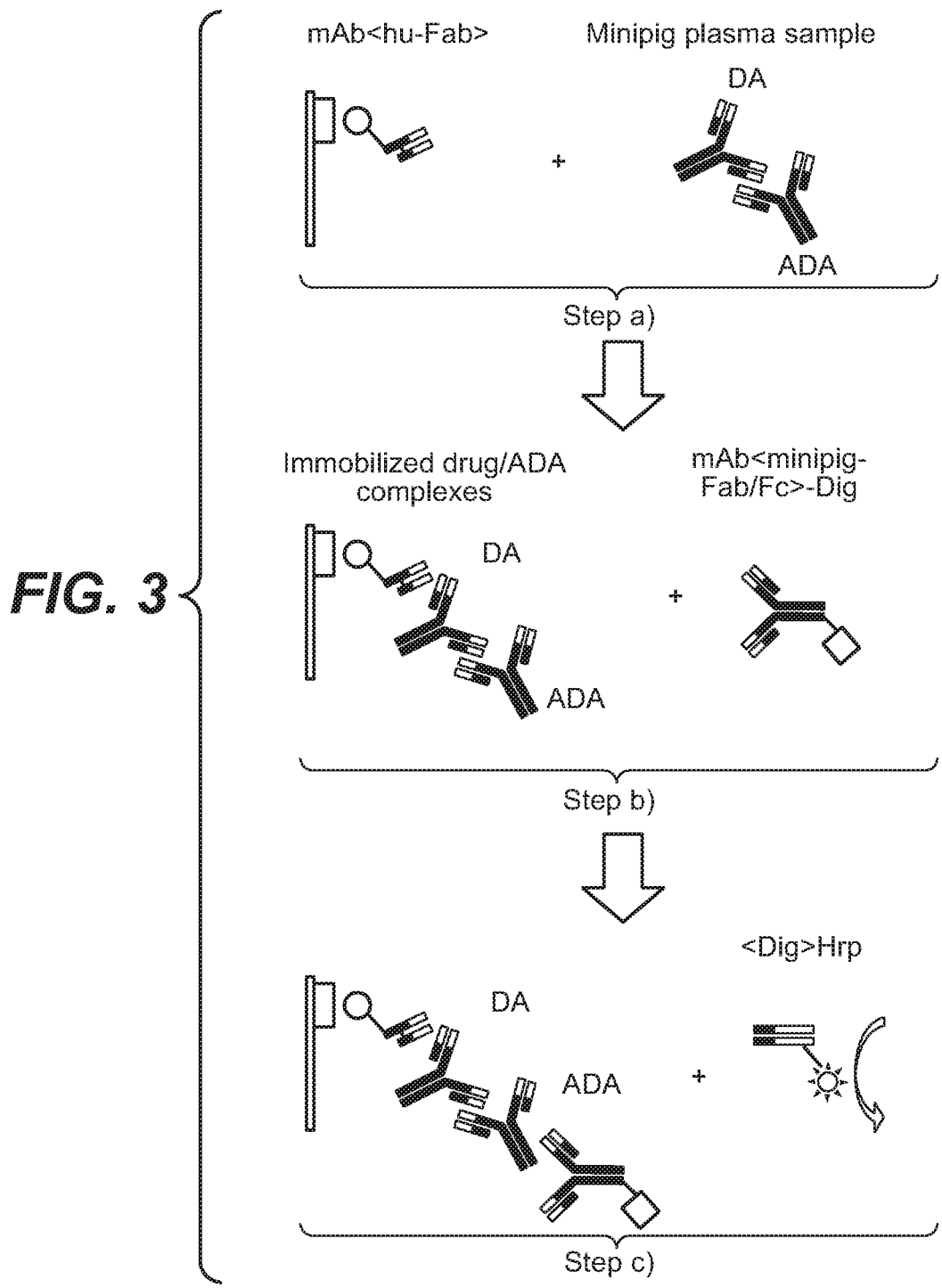
FIG. 3: Exemplified scheme of method for detection of drug/ADA complexes from a minipig sample (IC assay without pre-incubation) [method of the invention]

A scheme exemplifying this test system suitable for direct detection of drug/ADA complexes is shown in FIG. 3.

Figure 4:
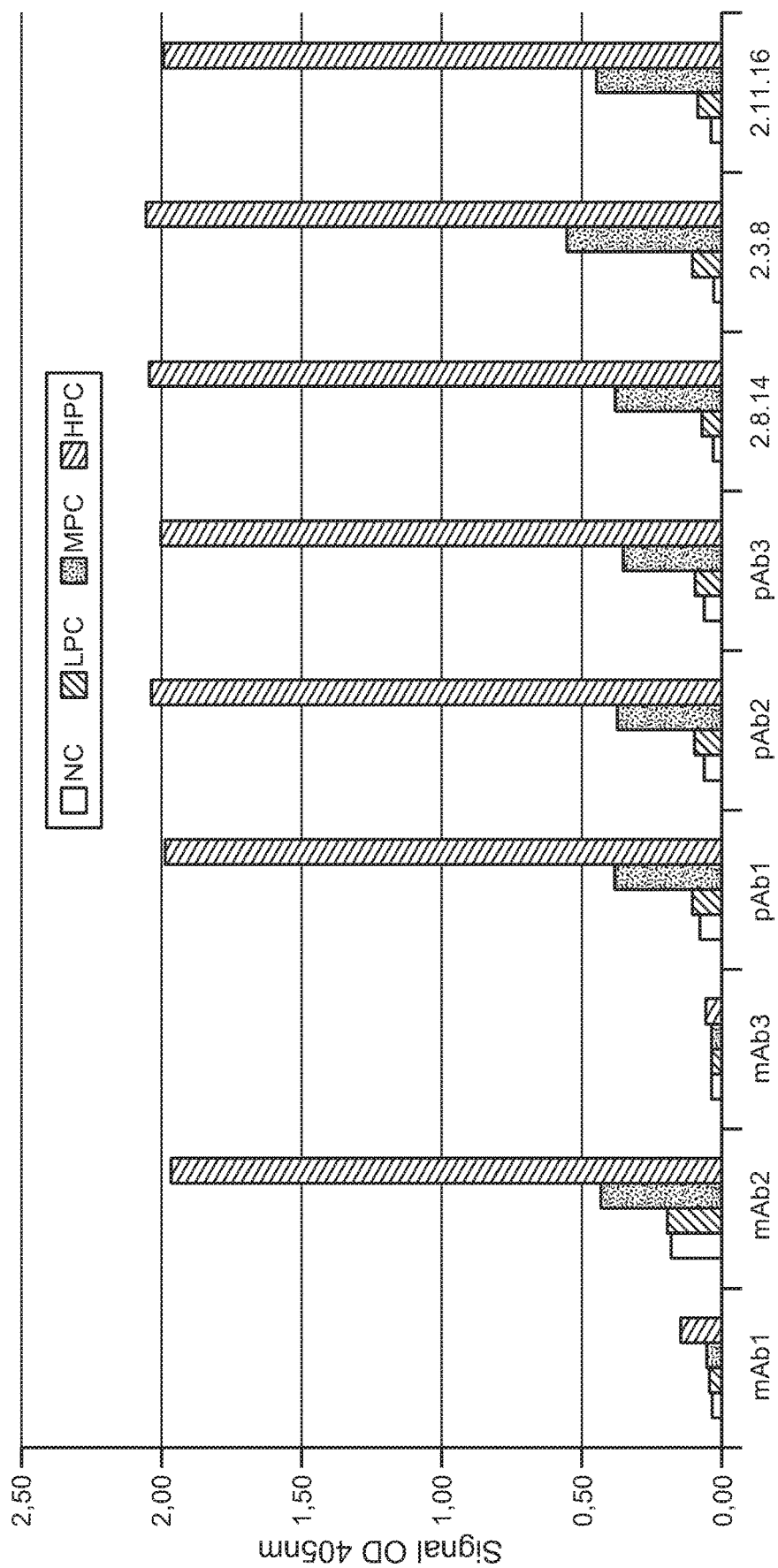
FIG. 4: Application of monoclonal anti-minipig IgG antibodies of the invention vs. commercially available anti-pig IgG antibodies in a method of the invention for detecting drug/ADA complexes in a minipig sample (IC assay without pre-incubation with drug). For description of experiment see Example 5.

Results are shown in FIG. 4, with "NC" referring to the negative control, "LPC" referring to the positive control with low levels of human IgG/swine IgG conjugates, "MPC" referring to the positive control with medium levels of human IgG/swine IgG conjugates; and "HPC" referring to the positive control with high levels of human IgG/swine IgG conjugates.

The tested commercially available monoclonal antibodies did either exhibit a rather high background (mAb2) or did not show significant signals at all (mAb1, mAb3). The tested commercially available polyclonal antibodies showed a reasonable signal-to-noise ratio and appear suitable for this detection method. All tested antibodies of the invention exhibited a signal-to-noise ratio slightly superior to the polyclonal antibodies that were tested.

Example 6

Applicability of Generated Monoclonal Anti-Minipig IgG Antibodies vs. Commercially Available Anti-Pig IgG Antibodies in a Method of the Invention for Detecting ADA in a Minipig Sample (with Pre-Incubation with Drug)

In order to assess the applicability of different anti-minipig IgG antibodies in a method of the invention for detection of ADA from a minipig sample the commercially available polyclonal antibodies as used in Example 5 were compared to antibodies of the invention.

For detection of ADA from a minipig sample, the following assay (according to the invention) was used:

Biotinylated anti-human IgG-Fab (kappa) monoclonal antibody MAb<h-IgG-kappa>M-1.7.10-Fab' was bound to the wells of a Streptavidin-coated microtiter plate (SA-MTP) in the first step. Excess of unbound Fab'—fragment was removed by washing.

Control samples were the used as described in Example 5 (LPC, MPC, HPC, and NC).

For analysis the control samples were added to and incubated in the wells of the microtiter plate. After washing away unbound substances the human IgG/swine IgG conjugates (mimicking drig/ADA complexes) were detected with the indicated digoxigenylated anti-minipig antibody followed by an incubation with a horse-radish peroxidase labeled anti-digoxigenin antibody. The antibody-enzyme conjugate catalyzes the color reaction of the ABTS® substrate. The signal was measured by ELISA reader at 405 nm wavelength (reference wavelength: 490 nm ([405/490] nm)). Absorbance values of each sample were determined in duplicates.

Figure 5:
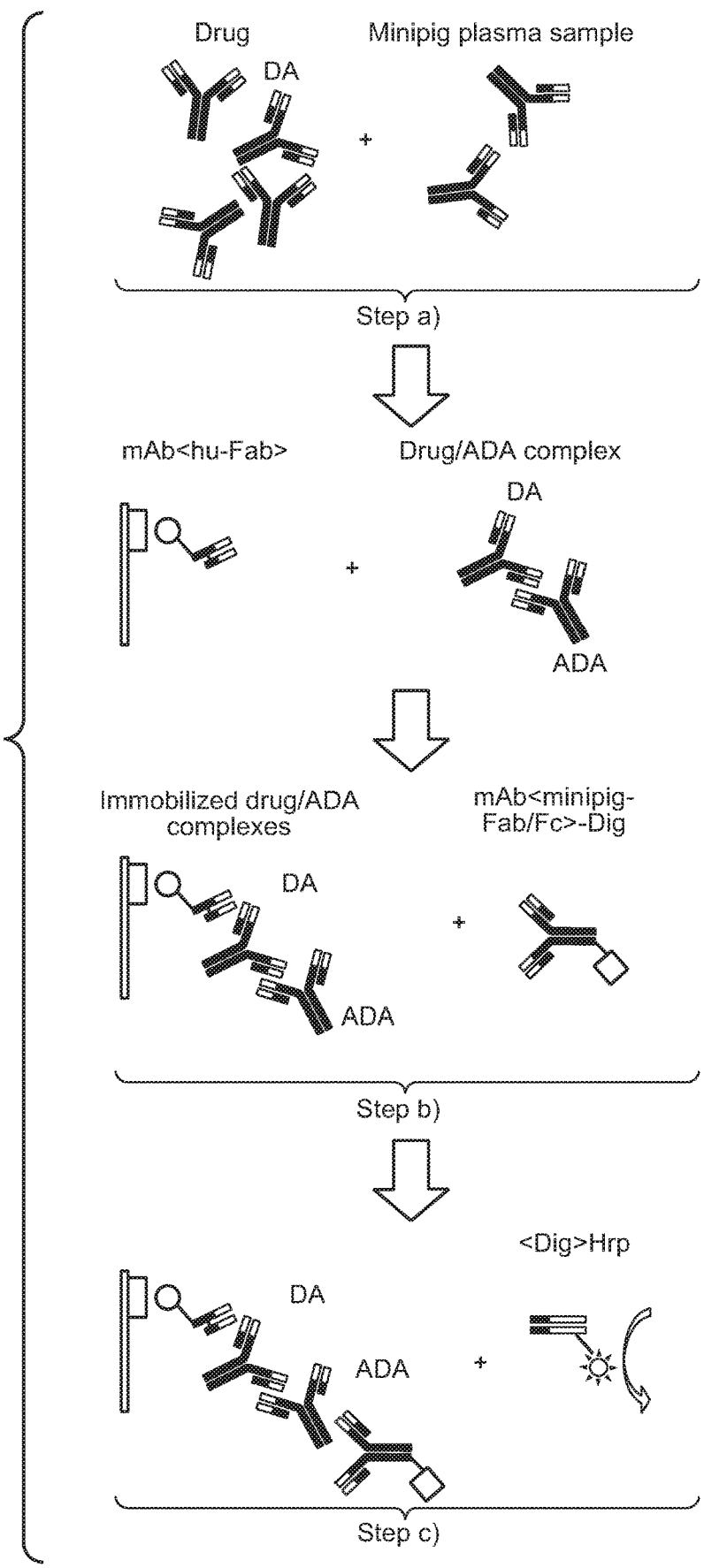
FIG. 5: Exemplified scheme of method for detection of ADA from a minipig sample (IC assay with pre-incubation) [method of the invention]

A scheme exemplifying this test system suitable for detection of ADA and drug/ADA complexes from minipig samples is shown in FIG. 5.

Figure 6:
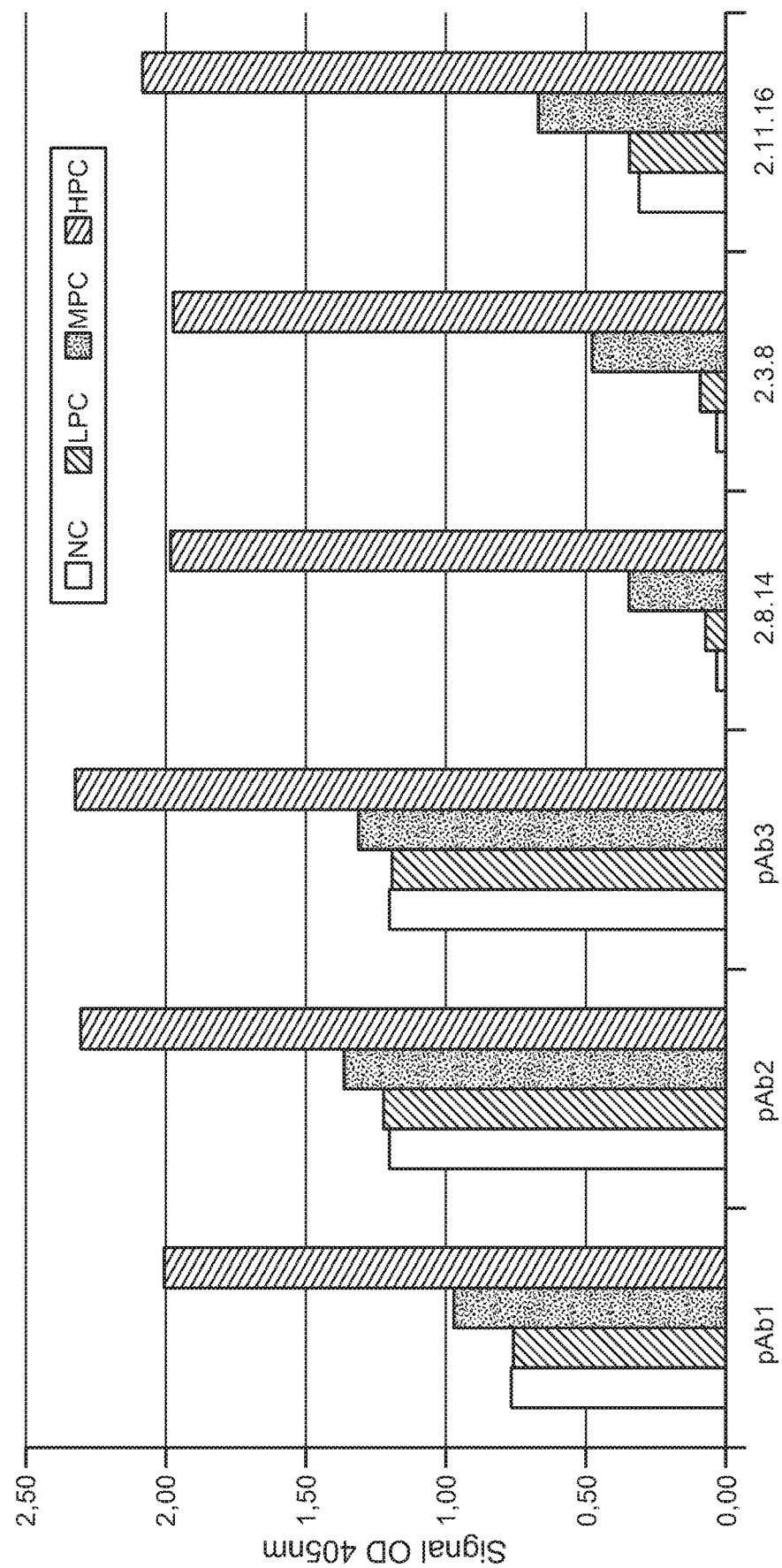
FIG. 6: Application of monoclonal anti-minipig IgG antibodies of the invention vs. commercially available anti-pig IgG antibodies in a method of the invention for detecting ADA in a minipig sample (IC assay with pre-incubation with drug). For description of experiment see Example 6.

Results are shown in FIG. 6, with "NC" referring to the negative control, "LPC" referring to the positive control with low levels of human IgG/swine IgG conjugates, "MPC" referring to the positive control with medium levels of human IgG/swine IgG conjugates; and "HPC" referring to the positive control with high levels of human IgG/swine IgG conjugates.

The tested commercially available polyclonal antibodies showed a low signal-to-noise ratio exhibiting a rather high background noise, which likely occurs due to cross-reactivity with human IgG. All tested antibodies of the invention exhibited a better signal-to-noise ratio than the prior art antibodies.

Example 7

Detection of ADA from Minipig Samples with a Method of the Invention Using Monoclonal Anti-Minipig IgG 2.8.14

Detection of ADA from minipig samples derived from different in vivo studies with human IgG1 drug antibodies was carried out with a method of the invention using monoclonal anti-minipig IgG 2.8.14.

The results were compared to a direct immunoassay for detecting ADA from minipig samples ("bridging assay") using an appropriately conjugated drug antibody for detection.

The bridging assay (comparative example) was carried out as follows:

In brief, the minipig sample, which is appropriately diluted, depending on the sample type, is pre-incubated with a biotinylated drug antibody as a capture antibody and a digoxigenin-coupled drug antibody at the same time. On a Streptavidin-coated microtiter plate the binding of ADA from the minipig sample to the biotin-coupled drug antibody and the digoxigenin-coupled drug antibody is detected by an incubation with a horse-radish peroxidase labeled anti-digoxigenin antibody. The antibody-enzyme conjugate catalyzes the color reaction of the ABTS® substrate. The signal was measured by ELISA reader at 405 nm wavelength (reference wavelength: 490 nm ([405/490] nm)).

The detection of ADA from the minipig samples with the method of the invention (further also referred to herein as "IC assay with pre-incubation") was carried out as described in Example 6 with the difference that instead of the previously screened minipig samples the indicated samples from in vivo studies were used and diluted in a 1:20 ratio. Minipig samples were taken from in vivo studies of two different ophthalmic drug antibodies, with drug A being a human full length IgG1 CrossMab and drug B being a human IgG1 Fab fragment.

As a positive control a human IgG (purified from human serum, in house preparation), which was chemically conjugated with swine IgG (purified from pig serum, in house preparation) spiked in 2% minipig CTAD plasma was used. Minipig pool plasma was used as a negative control.

Results are shown in Tables 2 to 10 which indicate, wherever applicable, the application route of the indicated drug and the dose, the sample type, subject identifier of the minipig that underwent the indicated treatment, the time of the sampling after applying the drug, and the result of the ADA detection (classified as positive [pos] and negative [neg]. A screening cut point (CP) was evaluated according to Shankar et al. (J Pharm Biomed Anal. 2008 Dec. 15; 48(5):1267-81) using a floating CP and non-parametric determination. By calculating a plate specific CP (blank of pooled naïve plasma multiplied by the normalization factor), screening negative (<plate-specific CP, PSCP) and screening positive (≥PSCP) samples were identified. Method validation was thoroughly performed according to the current guidelines. This was done for each one of the assays of the invention as well for the bridging assays used as a comparative example individually.

Figure 7:
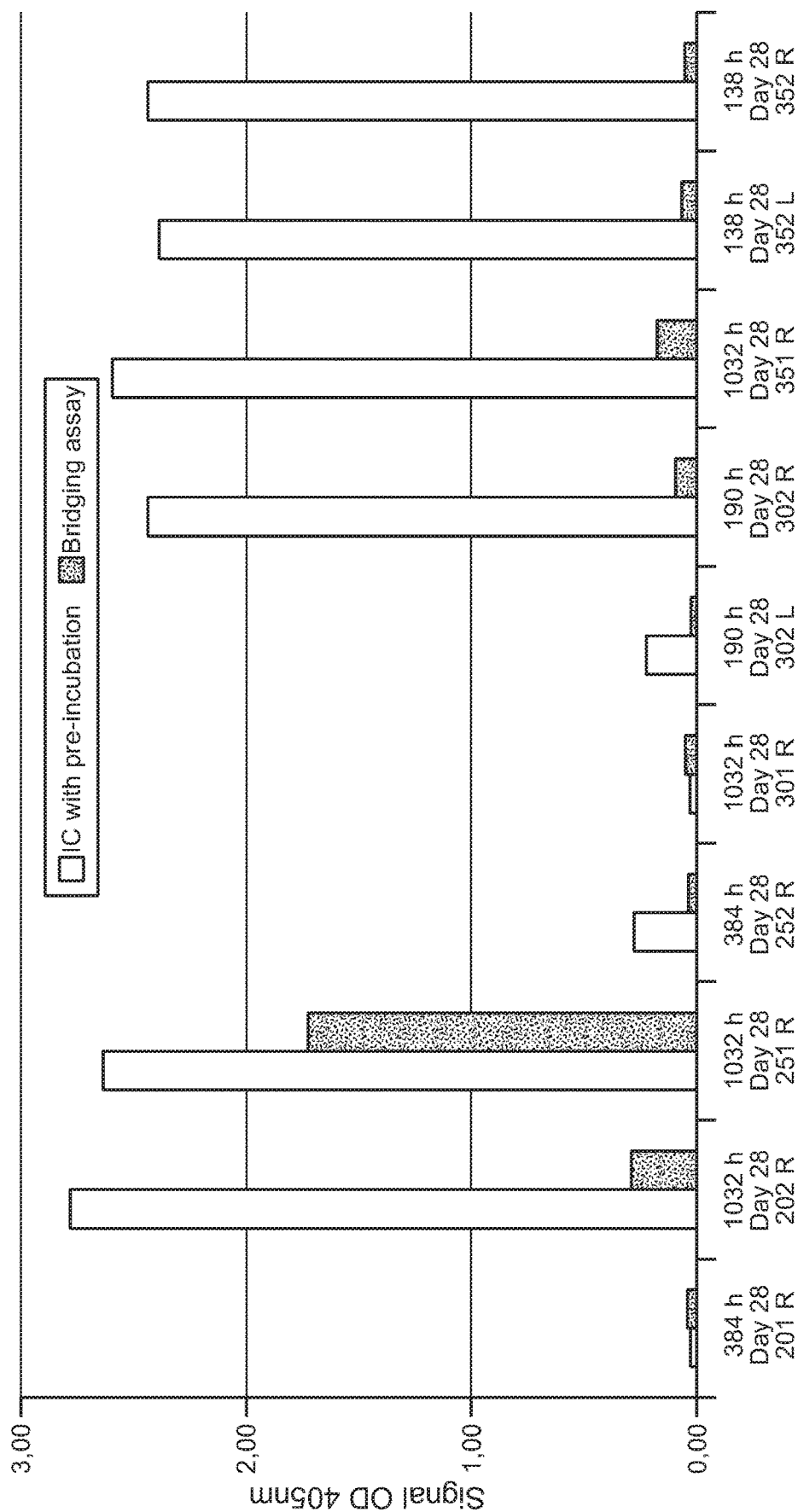
FIG. 7: Detection of ADA from minipig samples using a method of the invention (IC assay with pre-incubation with drug) compared to detection via a bridging assay as described in Example 7.

Results from the intravitreal injection of drug B as shown in Tables 7 and 9 further below for vitreous humor samples are also shown in FIG. 7 indicating the absolute OD values that were assessed with both assays.

TABLE 2

Intravitreal injection of 1.5 mg/eye drug A, plasma sample

| Subject | Hour Nominal | IC-Assay with pre-incubation ADA pos/neg | Bridging Assay (comparison) ADA pos/neg |
|---|---|---|---|
| A70108 | 12 h | neg | neg |
|  | 168 h | neg | neg |
| A70109 | 12 h | neg | neg |
|  | 72 h | neg | neg |

TABLE 2-continued

Intravitreal injection of 1.5 mg/eye drug A, plasma sample

| Subject | Hour Nominal | IC-Assay with pre-incubation ADA pos/neg | Bridging Assay (comparison) ADA pos/neg |
|---|---|---|---|
|  | 168 h | neg | pos |
|  | 336 h | pos | pos |
| A70110 | 12 h | neg | neg |
|  | 168 h | neg | neg |
|  | 336 h | pos | pos |
| A70111 | 12 h | neg | neg |
|  | 168 h | neg | neg |
|  | 336 h | pos | pos |
|  | 504 h | pos | pos |
|  | 672 h | pos | pos |
| A70112 | 12 h | neg | neg |
|  | 168 h | neg | neg |
|  | 336 h | pos | pos |
|  | 504 h | pos | pos |
|  | 672 h | pos | pos |

TABLE 3

Intravitreal injection of 1.5 mg/eye drug A, vitreous humor sample

| Subject | Eye | Hour Nominal | IC-Assay with pre-incubation ADA pos/neg | Bridging Assay (comparison) ADA pos/neg |
|---|---|---|---|---|
| A70107 | left | 168 h | neg | neg |
|  | right | 168 h | neg | neg |
| A70108 | left | 168 h | neg | neg |
|  | right | 168 h | neg | neg |
| A70109 | left | 336 h | pos | neg |
|  | right | 336 h | pos | neg |
| A70110 | left | 336 h | neg | neg |
|  | right | 336 h | pos | neg |
| A70111 | left | 672 h | neg | neg |
|  | right | 672 h | neg | neg |
| A70112 | left | 672 h | pos | neg |
|  | right | 672 h | pos | neg |

TABLE 4

Intravenous injection of 0.3 mg/kg drug A (human IgG1), plasma sample

| Subject | Hour Nominal | IC-Assay with pre-incubation ADA pos/neg | Bridging Assay (comparison) ADA pos/neg |
|---|---|---|---|
| A70125 | 0.5 h | neg | neg |
|  | 168 h | pos | neg |
|  | 336 h | pos | pos |
|  | 504 h | pos | pos |
|  | 672 h | pos | pos |
| A70126 | 0.5 h | neg | neg |
|  | 72 h | neg | neg |
|  | 168 h | pos | pos |
|  | 336 h | pos | pos |
|  | 504 h | pos | pos |
|  | 672 h | pos | pos |

TABLE 5

Intravitreal injection of 5 mg/eye drug B, plasma sample

| Subject | Dosing day | Hour Nominal | IC-Assay with pre-incubation ADA pos/neg | Bridging Assay (comparison) ADA pos/neg |
|---|---|---|---|---|
| 201 | 1 | 0 | neg | neg |
|  |  | 72 | neg | neg |
|  |  | 168 | neg | neg |
|  |  | 240 | neg | neg |
|  | 28 | 0 | pos | pos |
|  |  | 72 | pos | pos |
|  |  | 168 | pos | pos |
|  |  | 240 | pos | pos |
|  |  | after termination (day 71) | pos | pos |
| 202 | 1 | 4 | neg | — |
|  |  | 72 | neg | neg |
|  |  | 168 | neg | neg |
|  |  | 240 | pos | neg |
|  | 28 | 0 | pos | pos |
|  |  | 72 | pos | pos |
|  |  | 168 | pos | pos |
|  |  | 240 | pos | pos |
|  |  | 336 | pos | pos |
|  |  | after termination (day 71) | pos | pos |
| 251 | 1 | 0 | neg | neg |
|  |  | 72 | neg | neg |
|  |  | 168 | neg | neg |
|  |  | 240 | pos | pos |
|  | 28 | 0 | pos | pos |
|  |  | 168 | pos | pos |
|  |  | 240 | pos | pos |
|  |  | 336 | pos | pos |
|  |  | after termination (day 71) | pos | pos |
| 252 | 1 | 0 | neg | neg |
|  |  | 72 | neg | neg |
|  |  | 168 | neg | pos |
|  |  | 240 | pos | pos |
|  | 28 | 0 | pos | pos |
|  |  | 72 | pos | pos |
|  |  | 168 | pos | pos |
|  |  | 240 | pos | pos |
|  |  | after termination (day 71) | pos | pos |

TABLE 6

Intravitreal injection of 10 mg/eye drug B, plasma sample

| Subject | Dosing day | Hour Nominal | IC-Assay with pre-incubation ADA pos/neg | Bridging Assay (comparison) ADA pos/neg |
|---|---|---|---|---|
| 301 | 1 | 0 | neg | neg |
|  |  | 72 | neg | neg |
|  |  | 168 | neg | neg |
|  |  | 240 | neg | neg |
|  | 28 | 0 | pos | neg |
|  |  | 24 | pos | neg |
|  |  | 72 | pos | neg |
|  |  | 168 | pos | neg |
|  |  | 240 | pos | neg |
|  |  | 336 | pos | neg |
|  |  | after termination (day 71) | pos | pos |
| 302 | 1 | 0 | neg | neg |
|  |  | 72 | neg | neg |
|  |  | 168 | neg | neg |
|  |  | 240 | neg | neg |
|  | 28 | 0 | pos | pos |
|  |  | 4 | pos | — |
|  |  | 24 | pos | — |

TABLE 6-continued

Intravitreal injection of 10 mg/eye drug B, plasma sample

| Subject | Dosing day | Hour Nominal | IC-Assay with pre-incubation ADA pos/neg | Bridging Assay (comparison) ADA pos/neg |
|---|---|---|---|---|
| | | 72 | pos | pos |
| | | 168 | pos | pos |
| | | after termination (day 71) | pos | pos |
| 351 | 1 | 0 | neg | neg |
| | | 72 | neg | neg |
| | | 168 | neg | neg |
| | | 240 | neg | neg |
| | 28 | 0 | pos | pos |
| | | 24 | pos | — |
| | | 72 | pos | pos |
| | | 168 | pos | pos |
| | | 240 | pos | pos |
| | | 336 | pos | pos |
| | | after termination (day 71) | pos | pos |
| 352 | 1 | 0 | neg | neg |
| | | 72 | neg | neg |
| | | 168 | neg | neg |
| | | 240 | pos | pos |
| | 28 | 0 | pos | pos |
| | | 4 | pos | — |
| | | 24 | pos | — |
| | | 72 | pos | pos |
| | | after termination (day 71) | pos | pos |

TABLE 7

Intravitreal injection of 5 mg/eye drug B, vitreous humor sample

| Subject | Eye | Dosing day | Hour Nominal | IC-Assay with pre-incubation ADA pos/neg | Bridging Assay (comparison) ADA pos/neg |
|---|---|---|---|---|---|
| 201 | right | 28 | 384 | neg | neg |
| 202 | right | 28 | 1032 | pos | pos |
| 251 | right | 28 | 1032 | pos | pos |
| 252 | right | 28 | 384 | pos | neg |

TABLE 8

Intravitreal injection of 5 mg/eye drug B, aqueous humor sample

| Subject | Eye | Dosing day | Hour Nominal | IC-Assay with pre-incubation ADA pos/neg | Bridging Assay (comparison) ADA pos/neg |
|---|---|---|---|---|---|
| 201 | right | 1 | 168 | neg | neg |
| | | 28 | 168 | neg | neg |
| | | 28 | 384 | neg | neg |
| 202 | right | 1 | 168 | neg | neg |
| | | 28 | 168 | neg | neg |
| 251 | right | 1 | 168 | neg | neg |
| | | 28 | 168 | pos | neg |
| 252 | right | 28 | 384 | neg | neg |

TABLE 9

Intravitreal injection of 10 mg/eye drug B, vitreous humor sample

| Subject | Eye | Dosing day | Hour Nominal | IC-Assay with pre-incubation ADA pos/neg | Bridging Assay (comparison) ADA pos/neg |
|---|---|---|---|---|---|
| 301 | right | 28 | 1032 | neg | neg |
| 302 | left | 28 | 190 | pos | neg |
| 302 | right | 28 | 190 | pos | pos |
| 351 | right | 28 | 1032 | pos | pos |
| 352 | left | 28 | 138 | pos | pos |
| 352 | right | 28 | 138 | pos | neg |

TABLE 10

Intravitreal injection of 10 mg/eye drug B, aqueous humor sample

| Subject | Eye | Dosing day | Hour Nominal | IC-Assay with pre-incubation ADA pos/neg | Bridging Assay (comparison) ADA pos/neg |
|---|---|---|---|---|---|
| 301 | right | 28 | 168 | neg | neg |
| 302 | right | 28 | 168 | pos | pos |

In summary, the results demonstrate that the method of the invention reliably detects ADA from minipig samples. The IC Assay with pre-incubation appears to be more sensitive than the Bridging Assay as in some samples ADA are detected via the IC-Assay with pre-incubation (method of the invention) but not with the Bridging Assay.

Example 8

Comparative Study of Methods of the Invention: Detection of ADA in Minipig Samples using an IC Assay with Pre-Incubation and Detection of Drug/ADA Complexes using an IC Assay Without Pre-Incubation using Monoclonal Anti-Minipig IgG 2.8.14

Detection of ADA from minipig samples derived from different in vivo studies with human IgG1 drug antibodies was carried out with a method of the invention using monoclonal anti-minipig IgG 2.8.14 in an experimental setting as described in Example 7 (IC Assay with pre-incubation).

Detection of drug/ADA complexes from minipig samples derived from different in vivo studies with human IgG1 drug antibodies was carried out with another method of the invention using monoclonal anti-minipig IgG 2.8.14, i.e. a setting as described in Example 5 (this method, used for detection of in vivo formed drug/ADA complexes, is further referred to herein also as "IC Assay without pre-incubation"). Deviating from the setting as described in Example 5, instead of previously screened minipig samples with low, medium and high levels of drug/ADA complexes, samples from in vivo studies were used as indicted and diluted in a 1:20 ratio. Minipig samples were taken from in vivo studies of two different ophthalmic drug antibodies, with drug A being a human full length IgG1 CrossMab and drug B being a human IgG1 Fab fragment.

As a positive control a human IgG (purified from human serum, in house preparation), which was chemically conjugated with swine IgG (purified from pig serum, in house preparation) spiked in 2% minipig CTAD plasma was used. Minipig pool plasma was used as a negative control.

Results are shown in Tables 11 to 16 which indicate, wherever applicable, the application route of the indicated drug and the dose, the sample type, subject identifier of the minipig that underwent the indicated treatment, the time of the sampling after applying the drug, and the result of the ADA detection (classified as positive [pos] and negative [neg]). A screening cut point (CP) was evaluated according to Shankar et al. (J Pharm Biomed Anal. 2008 Dec. 15; 48(5):1267-81) using a floating CP and non-parametric determination. By calculating a plate specific CP (blank of pooled naïve plasma multiplied by the normalization factor), screening negative (<plate-specific CP, PSCP) and screening positive (≥PSCP) samples were identified. Method validation was thoroughly performed according to the current guidelines. This was done for each one of the assays of the invention as well for the bridging assays used as a comparative example individually.

TABLE 11

Intravitreal injection of 5 mg/eye drug B, plasma sample

| Subject | Dosing day | Hour Nominal | IC-Assay without pre-incubation ADA pos/neg | IC-Assay with pre-incubation ADA pos/neg |
|---|---|---|---|---|
| 201 | 1 | 0 | neg | neg |
|  |  | 72 | neg | neg |
|  |  | 168 | neg | neg |
|  |  | 240 | neg | neg |
|  | 28 | 0 | neg | pos |
|  |  | 72 | neg | pos |
|  |  | 168 | pos | pos |
|  |  | 240 | pos | pos |
|  |  | after termination (day 71) | pos | pos |
| 202 | 1 | 4 | neg | neg |
|  |  | 72 | neg | neg |
|  |  | 168 | neg | neg |
|  |  | 240 | neg | pos |
|  | 28 | 0 | pos | pos |
|  |  | 72 | pos | pos |
|  |  | 168 | pos | pos |
|  |  | 240 | pos | pos |
|  |  | 336 | pos | pos |
|  |  | after termination (day 71) | pos | pos |
| 251 | 1 | 0 | neg | neg |
|  |  | 72 | neg | neg |
|  |  | 168 | neg | neg |
|  |  | 240 | neg | pos |
|  | 28 | 0 | neg | pos |
|  |  | 168 | pos | pos |
|  |  | 240 | pos | pos |
|  |  | 336 | pos | pos |
|  |  | after termination (day 71) | neg | pos |
| 252 | 1 | 0 | neg | neg |
|  |  | 72 | neg | neg |
|  |  | 168 | neg | neg |
|  |  | 240 | neg | pos |
|  | 28 | 0 | neg | pos |
|  |  | 72 | pos | pos |
|  |  | 168 | pos | pos |
|  |  | 240 | pos | pos |
|  |  | after termination (day 71) | pos | pos |

TABLE 12

Intravitreal injection of 10 mg/eye drug B, plasma sample

| Subject | Dosing day | Hour Nominal | IC-Assay without pre-incubation ADA pos/neg | IC-Assay with pre-incubation ADA pos/neg |
|---|---|---|---|---|
| 301 | 1 | 0 | neg | neg |
|  |  | 72 | neg | neg |
|  |  | 168 | neg | neg |
|  |  | 240 | neg | neg |
|  | 28 | 0 | neg | pos |
|  |  | 24 | neg | pos |
|  |  | 72 | neg | pos |
|  |  | 168 | neg | pos |
|  |  | 240 | neg | pos |
|  |  | 336 | neg | pos |
|  |  | after termination (day 71) | neg | pos |
| 302 | 1 | 0 | neg | neg |
|  |  | 72 | neg | neg |
|  |  | 168 | neg | neg |
|  |  | 240 | neg | pos |
|  | 28 | 0 | pos | pos |
|  |  | 4 | pos | pos |
|  |  | 24 | pos | pos |
|  |  | 72 | pos | pos |
|  |  | 168 | pos | pos |
|  |  | after termination (day 71) | pos | pos |
| 351 | 1 | 0 | neg | neg |
|  |  | 72 | neg | neg |
|  |  | 168 | neg | neg |
|  |  | 240 | neg | neg |
|  | 28 | 0 | pos | pos |
|  |  | 24 | pos | pos |
|  |  | 72 | pos | pos |
|  |  | 168 | pos | pos |
|  |  | 240 | pos | pos |
|  |  | 336 | pos | pos |
|  |  | after termination (day 71) | pos | pos |
| 352 | 1 | 0 | neg | neg |
|  |  | 72 | neg | neg |
|  |  | 168 | neg | neg |
|  |  | 240 | pos | pos |
|  | 28 | 0 | neg | pos |
|  |  | 4 | pos | pos |
|  |  | 24 | pos | pos |
|  |  | 72 | pos | pos |
|  |  | after termination (day 71) | pos | pos |

TABLE 13

Intravitreal injection of 5 mg/eye drug B, vitreous humor sample

| Subject | Eye | Dosing day | Hour Nominal | IC-Assay without pre-incubation ADA pos/neg | IC-Assay with pre-incubation ADA pos/neg |
|---|---|---|---|---|---|
| 201 | right | 28 | 384 | neg | neg |
| 202 | right | 28 | 1032 | pos | pos |
| 251 | right | 28 | 1032 | pos | pos |
| 252 | right | 28 | 384 | pos | neg |

TABLE 14

Intravitreal injection of 5 mg/eye drug B, aqueous humor sample

| Subject | Eye | Dosing day | Hour Nominal | IC-Assay without pre-incubation ADA pos/neg | IC-Assay with pre-incubation ADA pos/neg |
|---|---|---|---|---|---|
| 201 | right | 1 | 168 | neg | neg |
|  |  | 28 | 168 | neg | neg |
|  |  | 28 | 384 | neg | neg |
| 202 | right | 1 | 168 | neg | neg |
|  |  | 28 | 168 | neg | neg |
| 251 | right | 1 | 168 | neg | neg |
|  |  | 28 | 168 | pos | pos |
| 252 | right | 28 | 384 | neg | neg |

TABLE 15

Intravitreal injection of 10 mg/eye drug B, vitreous humor sample

| Subject | Eye | Dosing day | Hour Nominal | IC-Assay without pre-incubation ADA pos/neg | IC-Assay with pre-incubation ADA pos/neg |
|---|---|---|---|---|---|
| 301 | right | 28 | 1032 | neg | neg |
| 302 | left | 28 | 190 | pos | pos |
| 302 | right | 28 | 190 | pos | pos |
| 351 | right | 28 | 1032 | pos | pos |
| 352 | left | 28 | 138 | pos | pos |
| 352 | right | 28 | 138 | pos | pos |

TABLE 16

Intravitreal injection of 10 mg/eye drug B, aqueous humor sample

| Subject | Eye | Dosing day | Hour Nominal | IC-Assay without pre-incubation ADA pos/neg | IC-Assay with pre-incubation ADA pos/neg |
|---|---|---|---|---|---|
| 301 | right | 28 | 168 | neg | neg |
| 302 | right | 28 | 168 | pos | pos |

The invention claimed is:

1. An in vitro method for determining the presence or absence of an anti-drug antibody (ADA) in a minipig sample, the method comprising:
   a) contacting the sample with an excess amount of a drug to which the ADA binds to form drug/ADA complexes,
   b) contacting the drug/ADA complexes with an antibody specifically binding minipig IgG selected from the an antibody comprising
      i. a CDR1 of the heavy chain of SEQ ID NO: 3, a CDR2 of the heavy chain of SEQ ID NO: 4, and a CDR3 of the heavy chain of SEQ ID NO: 5, and a CDR1 of the light chain of SEQ ID NO: 6, a CDR2 of the light chain of SEQ ID NO: 7, and a CDR3 of the light chain of SEQ ID NO: 8;
ii. a CDR1 of the heavy chain of SEQ ID NO: 19, a CDR2 of the heavy chain of SEQ ID NO: 20, and a CDR3 of the heavy chain of SEQ ID NO: 21, and a CDR1 of the light chain of SEQ ID NO: 22, a CDR2 of the light chain of SEQ ID NO: 23, and a CDR3 of the light chain of SEQ ID NO: 24; or
iii. a CDR1 of the heavy chain of SEQ ID NO: 27, a CDR2 of the heavy chain of SEQ ID NO: 28, and a CDR3 of the heavy chain of SEQ ID NO: 29, and a CDR1 of the light chain of SEQ ID NO: 30, a CDR2 of the light chain of SEQ ID NO: 31, and a CDR3 of the light chain of SEQ ID NO: 32; and
wherein the antibody specifically binding to minipig IgG does not bind to human IgG, and
c) determining the binding of the antibody specifically binding to minipig IgG to the drug/ADA complexes to determine whether ADA is present in the sample.

2. The method of claim 1, wherein in step a) the drug is immobilized on a support.

3. An in vitro method for determining the presence or absence of immune complexes comprising a drug and an antibody specifically binding to the drug (drug/ADA complexes) in a minipig sample, the method comprising:
a) contacting the minipig sample with an immobilized antibody that specifically binds to the drug to immobilize the drug/ADA complexes present in the minipig sample,
b) contacting the drug/ADA complexes with an antibody specifically binding minipig IgG selected from the an antibody comprising
i. a CDR1 of the heavy chain of SEQ ID NO: 3, a CDR2 of the heavy chain of SEQ ID NO: 4, and a CDR3 of the heavy chain of SEQ ID NO: 5, and a CDR1 of the light chain of SEQ ID NO: 6, a CDR2 of the light chain of SEQ ID NO: 7, and a CDR3 of the light chain of SEQ ID NO: 8;
ii. a CDR1 of the heavy chain of SEQ ID NO: 19, a CDR2 of the heavy chain of SEQ ID NO: 20, and a CDR3 of the heavy chain of SEQ ID NO: 21, and a CDR1 of the light chain of SEQ ID NO: 22, a CDR2 of the light chain of SEQ ID NO: 23, and a CDR3 of the light chain of SEQ ID NO: 24; or
iii. a CDR1 of the heavy chain of SEQ ID NO: 27, a CDR2 of the heavy chain of SEQ ID NO: 28, and a CDR3 of the heavy chain of SEQ ID NO: 29, and a CDR1 of the light chain of SEQ ID NO: 30, a CDR2 of the light chain of SEQ ID NO: 31, and a CDR3 of the light chain of SEQ ID NO: 32; and
wherein the antibody specifically binding to minipig IgG does not bind to human IgG, and
c) determining the binding of the antibody specifically binding to minipig IgG to the drug/ADA complexes to determine whether ADA is present in the sample.

4. The method of one of claim 1 or 3, wherein the antibody specifically binding to minipig IgG does not specifically bind to mouse IgG.

5. The method of claim 4, wherein the antibody specifically binding to minipig IgG comprises
a) a VH sequence of SEQ ID NO: 1 and a VL sequence of SEQ ID NO: 2;
b) a VH sequence of SEQ ID NO: 17 and a VL sequence of SEQ ID NO: 18; or
c) a VH sequence of SEQ ID NO: 25 and a VL sequence of SEQ ID NO: 26.

6. The method of claim 5, wherein the antibody specifically binding to minipig IgG specifically binds to the Fab domain of minipig IgG.

7. The method of claim 6, wherein the drug is a drug antibody (DA).

8. The method of claim 7, wherein the drug antibody is an human or humanized IgG antibody.

9. The method of claim 7, wherein the drug antibody is a Fab fragment.

10. The method of claim 8, wherein the method is a sandwich assay, wherein in step a) the drug/ADA complexes are contacted with an antibody specifically binding to human IgG, wherein the antibody specifically binding to human IgG is immobilized on a support, thereby immobilizing the drug/ADA complexes on the support, and
wherein the immobilized drug/ADA complexes are subsequently contacted with the antibody specifically binding to minipig IgG according to step b).

11. The method of claim 1, wherein the antibody specifically binding to minipig IgG is conjugated to a detectable label.

12. An antibody specifically binding to minipig IgG, comprising
a) a CDR1 of the heavy chain of SEQ ID NO: 3, a CDR2 of the heavy chain of SEQ ID NO: 4, and a CDR3 of the heavy chain of SEQ ID NO: 5, and a CDR1 of the light chain of SEQ ID NO: 6, a CDR2 of the light chain of SEQ ID NO: 7, and a CDR3 of the light chain of SEQ ID NO: 8;
b) comprises a CDR1 of the heavy chain of SEQ ID NO: 19, a CDR2 of the heavy chain of SEQ ID NO: 20, and a CDR3 of the heavy chain of SEQ ID NO: 21, and a CDR1 of the light chain of SEQ ID NO: 22, a CDR2 of the light chain of SEQ ID NO: 23, and a CDR3 of the light chain of SEQ ID NO: 24; or
c) a CDR1 of the heavy chain of SEQ ID NO: 27, a CDR2 of the heavy chain of SEQ ID NO: 28, and a CDR3 of the heavy chain of SEQ ID NO: 29, and a CDR1 of the light chain of SEQ ID NO: 30, a CDR2 of the light chain of SEQ ID NO: 31, and a CDR3 of the light chain of SEQ ID NO: 32.

13. The antibody of claim 12, wherein the antibody is selected from
a) an antibody comprising a VH sequence having at least 95% sequence identity to the amino acid sequence of SEQ ID NO: 1; and a VL sequence having at least 95% sequence identity to the amino acid sequence of SEQ ID NO: 2;
b) an antibody comprising a VH sequence having at least 95% sequence identity to the amino acid sequence of SEQ ID NO: 17; and a VL sequence having at least 95% sequence identity to the amino acid sequence of SEQ ID NO: 18; or
c) an antibody comprising a VH sequence having at least 95% sequence identity to the amino acid sequence of SEQ ID NO: 25; and a VL sequence having at least 95% sequence identity to the amino acid sequence of SEQ ID NO: 26.

14. The antibody of claim 12 wherein the antibody is capable of determining the presence or absence of an anti-drug antibody (ADA) in a minipig sample.

15. The method of claim 9, wherein the method is a sandwich assay, wherein in step a) the drug/ADA complexes are contacted with an antibody specifically binding to human IgG, wherein the antibody specifically binding to human IgG is immobilized on a support, thereby immobilizing the drug/ADA complexes on the support, and wherein the immobilized drug/ADA complexes are subsequently contacted with the antibody specifically binding to minipig IgG according to step b).

* * * * *

SEQUENCE LISTING

```
<160> NUMBER OF SEQ ID NOS: 32

<210> SEQ ID NO 1
<211> LENGTH: 123
<212> TYPE: PRT
<213> ORGANISM: Mus musculus

<400> SEQUENCE: 1

Gln Ala Tyr Leu Gln Gln Ser Gly Ala Glu Leu Val Arg Pro Gly Ala
1               5                   10                  15

Ser Val Lys Met Ser Cys Lys Ser Gly Tyr Thr Phe Leu Arg Tyr
            20                  25                  30

Asn Ile His Trp Leu Lys Gln Thr Pro Arg Gln Gly Leu Glu Trp Ile
        35                  40                  45

Gly Gly Val Tyr Thr Gly Asn Gly Asn Pro Ser Tyr Asn Gln Lys Phe
    50                  55                  60

Lys Asp Lys Ala Thr Leu Thr Val Asp Ser Ser Ser Thr Ala Tyr
65                  70                  75                  80

Met Gln Leu Ile Ser Leu Thr Ser Glu Asp Ser Ala Val Tyr Phe Cys
                85                  90                  95

Ala Arg Trp Gly Pro Tyr His Gly Ser Leu Glu Tyr Phe Phe Asp Tyr
            100                 105                 110

Trp Gly Gln Gly Thr Leu Leu Thr Val Ser Ser
        115                 120

<210> SEQ ID NO 2
<211> LENGTH: 112
<212> TYPE: PRT
<213> ORGANISM: Mus musculus

<400> SEQUENCE: 2

Asp Val Val Leu Thr Gln Thr Pro Leu Thr Leu Ser Val Thr Ile Gly
```

```
            1               5                  10                  15
          Gln Pro Ala Ser Ile Ser Cys Lys Ser Ser Gln Ser Leu Leu Asp Ser
                         20                  25                  30

Asp Gly Glu Thr Tyr Leu Asn Trp Leu Leu Gln Arg Pro Gly Gln Ser
                     35                  40                  45

Pro Lys Arg Leu Ile Tyr Leu Val Ser Glu Leu Asp Ser Gly Val Pro
                 50                  55                  60

Asp Arg Phe Thr Gly Ser Gly Ser Gly Thr Asp Phe Thr Leu Lys Ile
           65                  70                  75                  80

Ser Arg Val Glu Ala Glu Asp Leu Gly Ile Tyr Tyr Cys Trp Gln Gly
                             85                  90                  95

Thr His Phe Pro Gln Thr Phe Gly Gly Thr Lys Leu Glu Ile Lys
                         100                 105                 110
```

<210> SEQ ID NO 3
<211> LENGTH: 8
<212> TYPE: PRT
<213> ORGANISM: Mus musculus

<400> SEQUENCE: 3

Gly Tyr Thr Phe Leu Arg Tyr Asn
1               5

<210> SEQ ID NO 4
<211> LENGTH: 8
<212> TYPE: PRT
<213> ORGANISM: Mus musculus

<400> SEQUENCE: 4

Val Tyr Thr Gly Asn Gly Asn Pro
1               5

<210> SEQ ID NO 5
<211> LENGTH: 16
<212> TYPE: PRT
<213> ORGANISM: Mus musculus

<400> SEQUENCE: 5

Ala Arg Trp Gly Pro Tyr His Gly Ser Leu Glu Tyr Phe Phe Asp Tyr
1               5                   10                  15

<210> SEQ ID NO 6
<211> LENGTH: 11
<212> TYPE: PRT
<213> ORGANISM: Mus musculus

<400> SEQUENCE: 6

Gln Ser Leu Leu Asp Ser Asp Gly Glu Thr Tyr
1               5                   10

<210> SEQ ID NO 7
<211> LENGTH: 3
<212> TYPE: PRT
<213> ORGANISM: Mus musculus

<400> SEQUENCE: 7

Leu Val Ser
1

<210> SEQ ID NO 8
<211> LENGTH: 9
<212> TYPE: PRT

<213> ORGANISM: Mus musculus

<400> SEQUENCE: 8

Trp Gln Gly Thr His Phe Pro Gln Thr
1               5

<210> SEQ ID NO 9
<211> LENGTH: 117
<212> TYPE: PRT
<213> ORGANISM: Mus musculus

<400> SEQUENCE: 9

Asp Val Gln Leu Gln Glu Ser Gly Pro Gly Leu Val Lys Pro Ser Gln
1               5                   10                  15

Ser Leu Ser Leu Thr Cys Ser Val Thr Asp Tyr Ser Ile Thr Ser Gly
            20                  25                  30

Tyr Phe Trp Asn Trp Ile Arg Gln Phe Pro Gly Asn Lys Leu Glu Trp
        35                  40                  45

Met Gly Tyr Ile Thr Tyr Asp Gly Asn Asn Tyr Asn Pro Ser Leu
    50                  55                  60

Lys Ser Arg Leu Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Phe Cys
                85                  90                  95

Ala Arg Glu Ser Asn Asp Ala Met Asp Tyr Trp Gly Gln Gly Thr Ser
            100                 105                 110

Val Thr Val Ser Ser
        115

<210> SEQ ID NO 10
<211> LENGTH: 107
<212> TYPE: PRT
<213> ORGANISM: Mus musculus

<400> SEQUENCE: 10

Asp Ile Gln Met Thr Gln Ser Ser Tyr Leu Ser Val Ser Leu Gly
1               5                   10                  15

Gly Arg Val Thr Ile Ser Cys Glu Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45

Ser Gly Val Thr Ser Leu Glu Thr Gly Val Pro Ser Arg Phe Ser Gly
    50                  55                  60

Ser Gly Ser Gly Lys Asn Tyr Thr Leu Ser Ile Ala Ser Leu Gln Thr
65                  70                  75                  80

Glu Asp Val Ala Thr Tyr Tyr Cys Gln Gln Cys Trp Ser Ile Pro Tyr
                85                  90                  95

Thr Phe Gly Gly Gly Thr Lys Leu Glu Ile Lys
            100                 105

<210> SEQ ID NO 11
<211> LENGTH: 9
<212> TYPE: PRT
<213> ORGANISM: Mus musculus

<400> SEQUENCE: 11

Asp Tyr Ser Ile Thr Ser Gly Tyr Phe
1               5

<210> SEQ ID NO 12
<211> LENGTH: 7
<212> TYPE: PRT
<213> ORGANISM: Mus musculus

<400> SEQUENCE: 12

Ile Thr Tyr Asp Gly Asn Asn
1               5

<210> SEQ ID NO 13
<211> LENGTH: 10
<212> TYPE: PRT
<213> ORGANISM: Mus musculus

<400> SEQUENCE: 13

Ala Arg Glu Ser Asn Asp Ala Met Asp Tyr
1               5                   10

<210> SEQ ID NO 14
<211> LENGTH: 6
<212> TYPE: PRT
<213> ORGANISM: Mus musculus

<400> SEQUENCE: 14

Asp His Ile Asn Asn Trp
1               5

<210> SEQ ID NO 15
<211> LENGTH: 3
<212> TYPE: PRT
<213> ORGANISM: Mus musculus

<400> SEQUENCE: 15

Gly Val Thr
1

<210> SEQ ID NO 16
<211> LENGTH: 9
<212> TYPE: PRT
<213> ORGANISM: Mus musculus

<400> SEQUENCE: 16

Gln Gln Cys Trp Ser Ile Pro Tyr Thr
1               5

<210> SEQ ID NO 17
<211> LENGTH: 119
<212> TYPE: PRT
<213> ORGANISM: Mus musculus

<400> SEQUENCE: 17

Glu Val Arg Leu Val Glu Ser Gly Gly Gly Leu Val Lys Pro Gly Gly
1               5                   10                  15

Ser Leu Lys Leu Ser Cys Ala Ala Ser Gly Phe Pro Phe Ser Asp Tyr
            20                  25                  30

Ala Met Ser Trp Val Arg Gln Thr Pro Glu Lys Arg Leu Glu Trp Val
        35                  40                  45

Ala Gly Ile Asn Ser Asn Gly Gly Ala Thr Tyr Tyr Pro Asp Thr Val
    50                  55                  60

Lys Asp Arg Phe Thr Ile Ser Arg Asp Ser Ala Lys Asn Thr Leu Tyr
65                  70                  75                  80

Leu Gln Met Ser Ser Leu Arg Ser Glu Asp Thr Ala Ser Tyr Tyr Cys

```
                    85                  90                  95

Thr Arg His Gly Leu Leu Asp Trp Tyr Phe Asp Val Trp Gly Ala Gly
                100                 105                 110

Thr Thr Val Thr Val Ser Ser
            115

<210> SEQ ID NO 18
<211> LENGTH: 107
<212> TYPE: PRT
<213> ORGANISM: Mus musculus

<400> SEQUENCE: 18

Asp Ile Gln Met Thr Gln Ser Pro Ala Ser Leu Ser Ala Ser Val Gly
1               5                   10                  15

Glu Ser Val Thr Ile Thr Cys Arg Ala Ser Glu Gly Val Asn Asn Tyr
            20                  25                  30

Leu Ala Trp Tyr Gln His Arg Gln Gly Lys Ser Pro Gln Leu Leu Val
        35                  40                  45

Tyr Asn Ala Glu Thr Leu Ala Glu Gly Val Pro Ser Arg Phe Ser Gly
    50                  55                  60

Ser Gly Ser Gly Thr Gln Phe Ser Leu Lys Ile Ser Ser Leu Gln Pro
65                  70                  75                  80

Glu Asp Phe Gly Lys Tyr Val Cys Gln His His Tyr Gly Pro Pro Pro
                85                  90                  95

Thr Phe Gly Gly Gly Thr Lys Leu Glu Ile Arg
                100                 105

<210> SEQ ID NO 19
<211> LENGTH: 8
<212> TYPE: PRT
<213> ORGANISM: Mus musculus

<400> SEQUENCE: 19

Gly Phe Pro Phe Ser Asp Tyr Ala
1               5

<210> SEQ ID NO 20
<211> LENGTH: 8
<212> TYPE: PRT
<213> ORGANISM: Mus musculus

<400> SEQUENCE: 20

Ile Asn Ser Asn Gly Gly Ala Thr
1               5

<210> SEQ ID NO 21
<211> LENGTH: 12
<212> TYPE: PRT
<213> ORGANISM: Mus musculus

<400> SEQUENCE: 21

Thr Arg His Gly Leu Leu Asp Trp Tyr Phe Asp Val
1               5                   10

<210> SEQ ID NO 22
<211> LENGTH: 6
<212> TYPE: PRT
<213> ORGANISM: Mus musculus

<400> SEQUENCE: 22

Glu Gly Val Asn Asn Tyr
```

<210> SEQ ID NO 23
<211> LENGTH: 3
<212> TYPE: PRT
<213> ORGANISM: Mus musculus

<400> SEQUENCE: 23

Asn Ala Glu
1

<210> SEQ ID NO 24
<211> LENGTH: 9
<212> TYPE: PRT
<213> ORGANISM: Mus musculus

<400> SEQUENCE: 24

Gln His His Tyr Gly Pro Pro Pro Thr
1               5

<210> SEQ ID NO 25
<211> LENGTH: 115
<212> TYPE: PRT
<213> ORGANISM: Mus musculus

<400> SEQUENCE: 25

Gln Val Gln Leu Gln Gln Ser Gly Ala Glu Leu Met Lys Pro Gly Ala
1               5                   10                  15

Ser Val Lys Ile Ser Cys Lys Val Thr Gly Tyr Thr Phe Ser Asn Tyr
                20                  25                  30

Trp Ile Glu Trp Val Lys Gln Arg Pro Gly His Gly Leu Glu Trp Ile
            35                  40                  45

Gly Glu Ile Phe Pro Glu Ser Gly Gly Thr Thr Phe Asn Glu Lys Phe
        50                  55                  60

Lys Gly Lys Ala Thr Ile Thr Val Asp Thr Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Leu Pro Tyr Phe Asp Tyr Trp Gly Gln Gly Thr Thr Leu Thr
            100                 105                 110

Val Ser Ser
        115

<210> SEQ ID NO 26
<211> LENGTH: 106
<212> TYPE: PRT
<213> ORGANISM: Mus musculus

<400> SEQUENCE: 26

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
                20                  25                  30

Val Ser Trp Tyr Gln Gln Lys Pro Glu Gln Ser Pro Lys Leu Leu Ile
            35                  40                  45

Tyr Gly Ala Ser Asn Arg Tyr Thr Gly Val Pro Asp Arg Phe Thr Gly
        50                  55                  60

Ser Gly Ser Ala Thr Asp Phe Thr Leu Thr Ile Ser Ser Val Gln Ser
65                  70                  75                  80

```
Glu Asp Leu Ala Asp Tyr Tyr Cys Val Gln Ser His Arg Tyr His Ser
                85                  90                  95

Phe Gly Ser Gly Thr Lys Leu Glu Ile Lys
            100                 105

<210> SEQ ID NO 27
<211> LENGTH: 8
<212> TYPE: PRT
<213> ORGANISM: Mus musculus

<400> SEQUENCE: 27

Gly Tyr Thr Phe Ser Asn Tyr Trp
1               5

<210> SEQ ID NO 28
<211> LENGTH: 8
<212> TYPE: PRT
<213> ORGANISM: Mus musculus

<400> SEQUENCE: 28

Ile Phe Pro Glu Ser Gly Gly Thr
1               5

<210> SEQ ID NO 29
<211> LENGTH: 8
<212> TYPE: PRT
<213> ORGANISM: Mus musculus

<400> SEQUENCE: 29

Ala Arg Leu Pro Tyr Phe Asp Tyr
1               5

<210> SEQ ID NO 30
<211> LENGTH: 6
<212> TYPE: PRT
<213> ORGANISM: Mus musculus

<400> SEQUENCE: 30

Glu Asn Val Gly Thr Tyr
1               5

<210> SEQ ID NO 31
<211> LENGTH: 3
<212> TYPE: PRT
<213> ORGANISM: Mus musculus

<400> SEQUENCE: 31

Gly Ala Ser
1

<210> SEQ ID NO 32
<211> LENGTH: 8
<212> TYPE: PRT
<213> ORGANISM: Mus musculus

<400> SEQUENCE: 32

Val Gln Ser His Arg Tyr His Ser
1               5
```